US006074646A

United States Patent [19]
Cloyd et al.

[11] Patent Number: 6,074,646
[45] Date of Patent: Jun. 13, 2000

[54] NONDENATURED HIV ENVELOPE ANTIGENS FOR DETECTING EARLY HIV-SPECIFIC ANTIBODIES

[75] Inventors: Miles W. Cloyd, Galveston, Tex.; Keith M. Ramsey, Mobile, Ala.

[73] Assignee: Board of Regents, The University of Texas System, Austin, Tex.

[21] Appl. No.: 08/728,122

[22] Filed: Oct. 9, 1996

Related U.S. Application Data

[63] Continuation-in-part of application No. 08/143,168, Oct. 26, 1993, Pat. No. 5,587,285.

[51] Int. Cl.[7] .............................. A61K 39/21; C07K 1/00
[52] U.S. Cl. .................................... 424/188.1; 424/208.1; 530/350
[58] Field of Search ............................. 424/184.1–188.1; 530/350

[56] References Cited

U.S. PATENT DOCUMENTS

| | | | |
|---|---|---|---|
| 4,722,888 | 2/1988 | Broder et al. | 435/5 |
| 4,725,669 | 2/1988 | Essex et al. | 530/322 |
| 5,156,949 | 10/1992 | Luciw et al. | 435/5 |
| 5,587,285 | 12/1996 | Cloyd et al. | 435/5 |

OTHER PUBLICATIONS

Archibald et al., "Detection of salivary immunoglobulin A antibodies to HIV–1 in infants and children," *AIDS*, 4:417–420, 1990.

Hu et al., "Flow cytometric immunofluorescence assay for detection of antibodies to human immunodeficiency virus type 1 using insoluble precursor forms of recombinant polyproteins as carriers and antigens," *J. Clin. Microbiol.*, 34(6):1412–1419, 1996.

International Search Report dated Feb. 20, 1998 (PCT/US9720281) (UTFG:196P).

Keler et al., "Development of T–cell lines expressing functional HIV–1 envelope glycoproteins for evaluation of immune responses in HIV–infected individuals," *Journal of Acquired Immune Deficiency Syndromes and Human Retrovirology*, 13:117–126, 1996.

(List continued on next page.)

*Primary Examiner*—Donald E. Adams
*Assistant Examiner*—Jeffrey S. Parkin
*Attorney, Agent, or Firm*—Arnold White & Durkee

[57] ABSTRACT

Recombinant human immunodeficiency virus antigens capable of immunologically identifying the presence of early anti-HIV antibodies are stably expressed in a number of cell lines. These antigens have several clinically important applications as non-hazardous tools in the detection of human immunodeficiency virus exposure/infection, and in screening methods for HIV infection in idiopathic chronic lymphopenia (ICL). These techniques are improved over existing immunologically based and PCR based detection methods, as they provide for the detection of infection/ exposure in samples determined to be negative by conventional forms of these types of assays that do not detect anti-HIV gp160 antibodies that react to conformational epitopes of HIV. The invention finds particular application in the detection of human immunodeficiency virus exposure/ infection in infants. The earlier detection of the described methods is provided through the preserved immunoreactivity of the described recombinant conformationally intact human immunodeficiency virus that is capable of detecting a class of "early" anti-human immunodeficiency virus antibody not previously detectable by standard Western Blot or ELISA methods. The human immunodeficiency virus gp160 envelope antigen comprises one of the specific recombinant antigens examined with clinical human samples in these improved screening methods.

14 Claims, 14 Drawing Sheets

OTHER PUBLICATIONS

Miller and Rosman, "Improved retroviral vectors for gene transfer and expression," *Biotechniques,* 7(9):980–991, 1989.

Prehm, Nickel and Prehm, "A mild purification method for polysaccharide binding membrane proteins: Phase seperation of digitonin extracts to isolate the hyaluronate synthase from Streptococcus sp. in active form," *Protein Expression and Purification,* 7:343–346, 1996.

Weiblen et al., "Early diagnosis of HIV infection in infants by detection of IgA HIV antibodies," *Lancet,* 335:988–990, 1990.

Martin et al., 1991, "Detection of infection with human immunodeficiency virus (HIV) type 1 in infants by an anti–HIV immunoglobulin A assay using recombinant proteins," J. Pediatr. 118:354–358.

Pasquali et al., 1990, "Immunogenicity and Epitope Mapping of a Recombinant Solbule gp160 fo the Human Immunodeficiency Virus Type I Envelope Glycoprotein," AIDS Res. Human Retro. 6(9):1107–1113.

Aiuti, et al., "Silent HIV Infection," *Vaccine,* 11(5):538–541, 1993.

Heredia, et al., "Idiopathic CD4$^+$ T Lymphocytopenia: A Review and Current Perspective," *Transfusion Medicine Reviews,* VIII (4):223–231, Oct. 1994.

Patijn, et al., "Prevention of Transmission of HIV by Organ and Tissue Transplantation," *Transplant International,* 6:165–172, 1993.

Brettler, D., et al., "Silent Human Immunodeficiency Virus Type 1 Infection: A Rare Occurrence in a High–Risk Heterosexual Population", *Blood,* 80 (9):2396–2400, 1992.

Busch, M., et al., "Time course of detection of viral and serologic markers preceding human immunodeficiency virus type 1 seroconversion: implications for screening of blood and tissue donors", *Transfusion,* 35(2):91–97.

Busch, M., et al., Risk of human immunodeficiency virus (HIV) transmission by blood transfusions before the implementation of HIB–1 antibody screening.

Celum, C., et al., "Indeterminate Human Immunodeficiency Virus Type 1 Western Blots: Seroconversion Risk, Specificity of Supplemental Tests, and an Algorithm for Evaluation", *J. Infectious Dis.,* 164:656–64, 1991.

Chesebro, B., et al., "Characterization of Monoclonal Antibodies Reactive with Murine Leukemia Viruses; Use in Analysis of Strains of Friend MCF and Friend Ecotropic Murine Leukemia Virus", *Virology,* 127:134–148, 1983.

Clerici, J., et al., "Exposure to Human Immunodeficiency Virus Type 1–Specific T Helper Cell Responses before Detection of Infection by Polymerase Chain Reaction and Serum antibodies", *J. Infect. Dis.,* 164:178–82, 1991.

Clerici, M., et al., "HIV–Specific T–Helper Activity in Seronegative Health Care workers Exposed to Contaminated Blood", *JAMA,* 271(1):42–46, 1994.

Cloyd, M., et al., Cell–Surface Antigens Associated with Recombinant Mink Cell Focus–Inducing Murine Leukemia Viruses, *J. Exp. Med,* 149:702–12, 1979.

Cloyd, M., et al., "MCF–Specific Murine Monoclonal Antibodies Made Against AKR–247 MCF Virus Recognize a Unique Determinant Associated with the gp70–p15 (E) Complex", *J. Virol.,* 41(3) :1112–17, 1982.

Cohen, N., et al., "Transmission of Retroviruses by Transfusion of Screened Blood in Patients Undergoing Cardiac Surgery", *N. Eng. J. Med.,* 320(19):1172–76, 1989.

Coutlee, F., et al., "Absence of Prolonged Immunosilent Infection With Human Immunodeficiency Virus in Individuals With High–Risk Behaviors", *Amer. J. of Med.,* 96:42–48, 1994.

Eble, B., et al., "Resolution of infection status of human immunodeficiency virus (HIV)–seroindeterminate donors and high–risk seronegative individuals with polymerase chain reaction and virus culture: absence of persistent silent HIV type 1 infection in a high–prevalence area", *Transfusion,* 32(6) :503–508, 1992.

Garbarg–Chenon, A., et al., "Virus isolation, polymerase chain reaction and in vitro antibody production for the diagnosis of pediatric human immunodeficiency virus infection", *J. Virol. Methods,* 42:117–126, 1993.

Gregg, M., ed., "Classification System for Human Immunodeficiency Virus (HIV) Infection in Children Under 13 Years of Age", *Morbidity and Mortality Weekly Report,* 36(15)225–37, 1987.

Jehuda–Cohen, T., et al., "Polyclonal B–cell activation reveals antibodies against human immunodeficiency virus type 1 (HIV–1) in HIV–1–seronegative individuals", *Proc. Natl. Acad. Sci. USA,* 87:3972–76, 1990.

Kyte, J., et al., "A Simple Method for Displaying the Hydropathic Character of a Protein", *J. Mol. Biol. ,* 157:105–132, 1982.

Lepri, A., et al., "HIV disease progression in 854 women and men infected through injecting drug use and heterosexual sex and followed for up to nine years from seroconversion", *BMJ,* 309:1537–42, 1994.

Martin, N., et al., "Detection of infection with human immunodeficiency virus (HIV) type 1 in infants by an anti–HIV immunoglobulin A assay using recombinant proteins", *J. of Pediatrics,* 118(3):354–358.

Mayer, K., et al., "Human T–Lymphotropic Virus Type III in High–Risk Antibody Negative Homosexual Men", *Annals of Internal Medicine,* 104:194–96, 1986.

McNultry, A., et al., "Acquired immunodeficiency without evidence of HIV infection: national retrospective survey", *BMJ,* 308:825–26, 1994.

Pan, L., et al., "Lack of Detection of Human Immunodeficiency Virus in Persistently Seronegative Homosexual Men with High or Medium Risks for Infection", *J. of Infect. Dis.,* 164:962–64, 1991.

Pepose, J., et al., "New Developments in Serologic Screening of Corneal Donors for HIV–1 and Hepatitis B Virus Infections", *Ophthalmology,* 99(6):879–88, 1992.

Pezzella, M., et al., "Persistence of HIV–1 Silent Infection in Seronegative Subjects at High Risk", *J. Med. Virol.,* 35:14–18, 1991.

Portis, J., et al., "Monoclonal Antibodies to Xenotropic and MCG Murine Leukemia Viruses Derived during the Graft–versus–Host Reaction", *Virology,* 118:181–190, 1982.

Sambrook, J., et al., Immunoprecipitation of the Target Protein, *Molecular Cloning Laboratory Manual,* 18.44, 1989.

Sheppard, H., et al., "HIV–1 PCR and Isolation in Seroconverting and Seronegative Homosexual Men: Absence of Long–term Immunosilent Infection", *J. of AIDS,* 6:1339–46, 1993.

Simonds, R., et al., "Transmission of Human Immunodeficiency Virus Type 1 From a Seronegative Organ and Tissue Donor", *N. Eng. J. of Med.,* 326(11) :726–32, 1992.

Stramer, S., et al., "Transmission of HIV by Blood transfusion", *N. Eng. J. of Med.,* 319(8):513–14, 1988.

Yerly, S., et al., "Absence of Chronic Human Immunodeficiency Virus Infection without Seroconversion in Intravenous Drug Users: A Prospective and Retrospective Study", *JID,* 164:965–68, 1991.

Ward, J., et al., "Transmission of Human Immunodeficiency Virus (HIV) by Blood Transfusions Screened as Negative for HIV Antibody", *N. Eng. J. of Med.,* 318(8):473–478, 1988.

Report of a Consensus Workshop, Siena, Italy, Jan. 17–18, 1992: "Early Diagnosis of HIV Infection in Infants", *J. of AIDS,* 5:1169–78, 1992.

Gorrino, et al., "Detection of Human Immunodeficiency Virus Type 1 by PCR before Seroconversion in High–Risk Individuals Who Remain Seronegative for Prolonged Periods," *Eur. J. Clin. Microbiol. Infect. Dis.,* 13:271–276, 1994.

Gupta, et al., "Low Prevalence of HIV in High–Risk Seronegative Homosexual Men Evidenced by Virus Culture and Polymerase Chain Reaction," *AIDS,* 6(2):143–149, 1992.

Luque, et al., "Failure to Detect Silent HIV Infection by Polymerase Chain Reaction in Subjects at Risk for Heterosexually Transmitted HIV Type 1 Infection," *Eur. J. Clin. Microbiol. Infect. Dis.,* 12(9):663–667, Sep. 1993.

Muller et al., "Autoantibodies Typical of Non–Organ–Specific Autoimmune Diseases in HIV–Seropositive Patients," *AIDS,* 6(9):933–942, 1992.

```
                      10         20         30         40         50         60
                                            gtcgacatag cagaataggc gttactcgac agaggagagc
                                            sal I
         70         80         90        100        110        120
 aagaaatgga gccagtagat cctagactag agccctggaa gcatccagga agtcagccta
        130        140        150        160        170        180
 aaactgcttg taccaattgc tattgtaaaa agtgttgctt tcattgccaa gtttgtttca
        190        200        210        220        230        240
 taacaaaagc cttaggtatc tcctatggca ggaagaagcg gagacagcga cgaagagctc
        250        260        270        280        290        300
 atcagaacag tcagactcat caagtttctc tatcaaagca gtaagtagta catgtaacgc
        310        320        330        340        350        360
 aacctatacc aatagtaaca atagtagcct tagtagcagc aataataata gcaatagttg
```

FIG. 6A

```
         370        380        390        400        410        420
tgtggtccat agtaatcata gaatatagga aaatattaag acaaagaaaa atagacaggt 430        440        450        460        470        480
taattgatag actaatagaa agagcagaag acagtggcaa tgagagtgaa ggagaaatat 490        500        510        520        530        540
cagcacttgt ggagatgggg gtggagatgg ggcaccatgc tccttgggat gttgatgatc 550        560        570        580        590        600
tgtagtgcta cagaaaaatt gtgggtcaca gtctattatg gggtacctgt gtggaaggaa 610        620        630        640        650        660
gcaaccacca ctctattttg tgcatcagat gctaaagcat atgatacaga ggtacataat 670        680        690        700        710        720
gtttggacca cacatgcctg tgtacccaca gacccccaacc cacaagaagt agtattggta
```

FIG. 6B

```
     670        680        690        700        710        720
gtttggacca cacatgcctg tgtacccaca gaccccaacc cacaagaagt agtattggta 730        740        750        760        770        780
aatgtgacag aaaatttaa catgtggaaa aatgacatgg tagaacagat gcatgaggat 790        800        810        820        830        840
ataatcagtt tatgggatca aagcctaaag ccatgtgtaa aattaacccc actctgtgtt 850        860        870        880        890        900
agtttaaagt gcactgattt gaagaatgat actaatacca atagtagtag cgggagaatg 910        920        930        940        950        960
ataatggaga aaggagagat aaaaaactgc tctttcaata tcagcacaag caaaagaggt 970        980        990       1000       1010       1020
aaggtgcaga aagaatatgc atttttttat aaacttgata taataccaat agataatgat
```

FIG. 6C

```
      1030       1040       1050       1060       1070       1080
actaccagct atacgttgac aagttgtaac acctcagtca ttacacaggc ctgtccaaag 1090       1100       1110       1120       1130       1140
gtatcctttg agccaattcc catacattat tgtgccccgg ctggttttgc gattctaaaa 1150       1160       1170       1180       1190       1200
tgtaataata agacgttcaa tggaacagga ccatgtacaa atgtcagcac agtacaatgt 1210       1220       1230       1240       1250       1260
acacatggaa ttaggccagt agtatcaact caactgctgt taaatggcag tctagcagaa 1270       1280       1290       1300       1310       1320
gaagaggtag taattagatc tgtcaatttc acggacaatg ctaaaaccat aatagtacag 1330       1340       1350       1360       1370       1380
ctgaacacat ctgtagaaat taattgtaca agacccaaca acaatacaag aaaaaaatc
```

FIG. 6D

```
           1390       1400       1410       1420       1430       1440
cgtatccaga ggggaccagg gagagcattt gttacaatag gaaaaatagg aaatatgaga 1450       1460       1470       1480       1490       1500
caagcacatt gtaacattag tagagcaaaa tggaatgcca ctttaaaaca gatagctagc 1510       1520       1530       1540       1550       1560
aaattaagag aacaatttgg aaataataaa acaataatct ttaagcaatc ctcaggaggg 1570       1580       1590       1600       1610       1620
gacccagaaa ttgtaacgca cagttttaat tgtggagggg aatttttcta ctgtaattca 1630       1640       1650       1660       1670       1680
acacaactgt ttaatagtac ttggttttaat agtacttgga gtactgaagg gtcaaataac
```

FIG. 6E

```
     1690       1700       1710       1720       1730       1740
actgaaggaa gtgacacaat cacactccca tgcagaataa aacaatttat aaacatgtgg 1750       1760       1770       1780       1790       1800
caggaagtag gaaaagcaat gtatgcccct cccatcagtg gacaaattag atgttcatca 1810       1820       1830       1840       1850       1860
aatattacag ggctgctatt aacaagagat ggtggtaata gcaacaatga gtccgagatc 1870       1880       1890       1900       1910       1920
ttcagacctg gaggaggaga tatgagggac aattggagaa gtgaattata taaatataaa 1930       1940       1950       1960       1970       1980
gtagtaaaaa ttgaaccatt aggagtagca cccaccaagg caaagagaag agtggtgcag 1990       2000       2010       2020       2030       2040
agagaaaaaa gagcagtggg aataggagct ttgttccttg ggttcttgga agcagcagga
```

FIG. 6F

```
      2050       2060       2070       2080       2090       2100
agcactatgg gctgcacgtc aatgacgctg acggtacagg ccagacaatt attgtctggt 2110       2120       2130       2140       2150       2160
atagtgcagc agcagaacaa tttgctgagg gctattgagg cgcaacagca tctgttgcaa 2170       2180       2190       2200       2210       2220
ctcacagtct ggggcatcaa gcagctccag gcaagaatcc tggctgtgga aagataccta 2230       2240       2250       2260       2270       2280
aaggatcaac agctcctggg gatttggggt tgctctggaa aactcatttg caccactgct 2290       2300       2310       2320       2330       2340
gtgcccttga atgctagttg gagtaataaa tctctggaac agatttggaa taacatgacc 2350       2360       2370       2380       2390       2400
tggatggagt gggacagaga aattaacaat tacacaagct taatacactc cttaattgaa
```

FIG. 6G

```
       2410       2420       2430       2440       2450       2460
gaatcgcaaa accagcaaga aaagaatgaa caagaattat tggaattaga taaatgggca 2470       2480       2490       2500       2510       2520
agtttgtgga attggtttaa cataacaaat tggctgtggt atataaaatt attcataatg 2530       2540       2550       2560       2570       2580
atagtaggag gcttggtagg tttaagaata gtttttgctg tactttctgt agtgaataga 2590       2600       2610       2620       2630       2640
gttaggcagg gatattcacc attatcgttt cagacccacc tcccaacccc gagggaccc 2650       2660       2670       2680       2690       2700
gacaggcccg aaggaataga agaagaaggt ggagagagag acagagacag atccattcga 2710       2720
ttagtgaacg gatcct
          BamHI
```

FIG. 6H

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:

(A) LENGTH: 2730 base pairs
(B) TYPE: nucleic acid
(C) STRANDEDNESS: single
(D) TOPOLOGY: linear (xi) SEQUENCE DESCRIPTION: SEQ ID NO:1:

```
AACTGCTGTT TATCCATTTC AGAATTGGGT GTCGACATAG CAGAATAGGC GTTACTCGAC    60
AGAGGAGAGC AAGAAATGGA GCCAGTAGAT CCTAGACTAG AGCCCTGGAA GCATCCAGGA   120
AGTCAGCCTA AAACTGCTTG TACCAATTGC TATTGTAAAA AGTGTTGCTT TCATTGCCAA   180
GTTTGTTTCA TAACAAAAGC CTTAGGTATC TCCTATGGCA GGAAGAAGCG GAGACAGCGA   240
CGAAGAGCTC ATCAGAACAG TCAGACTCAT CAAGTTTCTC TATCAAAGCA GTAAGTAGTA   300
CATGTAACGC AACCTATACC AATAGTAACA ATAGTAGCCT TAGTAGCAGC AATAATAATA   360
GCAATAGTTG TGTGGTCCAT AGTAATCATA GAATATAGGA AAATATTAAG ACAAAGAAAA   420
ATAGACAGGT TAATTGATAG ACTAATAGAA AGAGCAGAAG ACAGTGGCAA TGAGAGTGAA   480
GGAGAAATAT CAGCACTTGT GGAGATGGGG GTGGAGATGG GGCACCATGC TCCTTGGGAT   540
GTTGATGATC TGTAGTGCTA CAGAAAAATT GTGGGTCACA GTCTATTATG GGGTACCTGT   600
GTGGAAGGAA GCAACCACCA CTCTATTTTG TGCATCAGAT GCTAAAGCAT ATGATACAGA   660
GGTACATAAT GTTTGGACCA CACATGCCTG TGTACCCACA GACCCCAACC CACAAGAAGT   720
AGTATTGGTA AATGTGACAG AAAATTTTAA CATGTGGAAA ATGACATGG TAGAACAGAT   780
GCATGAGGAT ATAATCAGTT TATGGGATCA AAGCCTAAAG CCATGTGTAA AATTAACCCC   840
ACTCTGTGTT AGTTTAAAGT GCACTGATTT GAAGAATGAT ACTAATACCA ATAGTAGTAG   900
CGGGAGAATG ATAATGGAGA AAGGAGAGAT AAAAAACTGC TCTTTCAATA TCAGCACAAG   960
CAAAAGAGGT AAGGTGCAGA AAGAATATGC ATTTTTTTAT AAACTTGATA TAATACCAAT  1020
AGATAATGAT ACTACCAGCT ATACGTTGAC AAGTTGTAAC ACCTCAGTCA TTACACAGGC  1080
CTGTCCAAAG GTATCCTTTG AGCCAATTCC CATACATTAT TGTGCCCCGG CTGGTTTTGC  1140
GATTCTAAAA TGTAATAATA AGACGTTCAA TGGAACAGGA CCATGTACAA ATGTCAGCAC  1200
AGTACAATGT ACACATGGAA TTAGGCCAGT AGTATCAACT CAACTGCTGT TAAATGGCAG  1260
TCTAGCAGAA GAAGAGGTAG TAATTAGATC TGTCAATTTC ACGGACAATG CTAAAACCAT  1320
AATAGTACAG CTGAACACAT CTGTAGAAAT TAATTGTACA AGACCCAACA ACAATACAAG  1380
AAAAAAAATC CGTATCCAGA GGGGACCAGG GAGAGCATTT GTTACAATAG GAAAAATAGG  1440
AAATATGAGA CAAGCACATT GTAACATTAG TAGAGCAAAA TGGAATGCCA CTTTAAAACA  1500
GATAGCTAGC AAATTAAGAG AACAATTTGG AAATAATAAA ACAATAATCT TTAAGCAATC  1560
CTCAGGAGGG GACCCAGAAA TTGTAACGCA CAGTTTTAAT TGTGGAGGGG AATTTTTCTA  1620
CTGTAATTCA ACACAACTGT TTAATAGTAC TTGGTTTAAT AGTACTTGGA GTACTGAAGG  1680
GTCAAATAAC ACTGAAGGAA GTGACACAAT CACACTCCCA TGCAGAATAA AACAATTTAT  1740
AAACATGTGG CAGGAAGTAG GAAAAGCAAT GTATGCCCCT CCCATCAGTG GACAAATTAG  1800
ATGTTCATCA AATATTACAG GGCTGCTATT AACAAGAGAT GGTGGTAATA GCAACAATGA  1860
GTCCGAGATC TTCAGACCTG GAGGAGGAGA TATGAGGGAC AATTGGAGAA GTGAATTATA  1920
TAAATATAAA GTAGTAAAAA TTGAACCATT AGGAGTAGCA CCCACCAAGG CAAAGAGAAG  1980
AGTGGTGCAG AGAGAAAAAA GAGCAGTGGG AATAGGAGCT TGTTCCTTG GGTTCTTGGG  2040
AGCAGCAGGA AGCACTATGG GCTGCACGTC AATGACGCTG ACGGTACAGG CCAGACAATT  2100
ATTGTCTGGT ATAGTGCAGC AGCAGAACAA TTTGCTGAGG GCTATTGAGG CGCAACAGCA  2160
```

```
                                                         -continued

TCTGTTGCAA  CTCACAGTCT  GGGGCATCAA  GCAGCTCCAG  GCAAGAATCC  TGGCTGTGGA    2220

AAGATACCTA  AAGGATCAAC  AGCTCCTGGG  GATTTGGGGT  TGCTCTGGAA  AACTCATTTG    2280

CACCACTGCT  GTGCCTTGGA  ATGCTAGTTG  GAGTAATAAA  TCTCTGGAAC  AGATTTGGAA    2340

TAACATGACC  TGGATGGAGT  GGGACAGAGA  AATTAACAAT  TACACAAGCT  TAATACACTC    2400

CTTAATTGAA  GAATCGCAAA  ACCAGCAAGA  AAAGAATGAA  CAAGAATTAT  TGGAATTAGA    2460

TAAATGGGCA  AGTTTGTGGA  ATTGGTTTAA  CATAACAAAT  TGGCTGTGGT  ATATAAAATT    2520

ATTCATAATG  ATAGTAGGAG  GCTTGGTAGG  TTTAAGAATA  GTTTTTGCTG  TACTTTCTGT    2580

AGTGAATAGA  GTTAGGCAGG  GATATTCACC  ATTATCGTTT  CAGACCCACC  TCCCAACCCC    2640

GAGGGGACCC  GACAGGCCCG  AAGGAATAGA  AGAAGAAGGT  GGAGAGAGAG  ACAGAGACAG    2700

ATCCATTCGA  TTAGTGAACG  GATCCTTAGC                                       2730
```

NONDENATURED HIV ENVELOPE ANTIGENS FOR DETECTING EARLY HIV-SPECIFIC ANTIBODIES

This application is a continuation-in-part of U.S. Ser. No. 08/143,168, filed Oct. 26, 1993, now U.S. Pat No. 5,587,285 which is incorporated by reference herein.

The government owns rights in the present invention pursuant to grant number ROI-AI32444 from the National Institutes of Health.

BACKGROUND OF THE INVENTION

I. Field of the Invention

The present invention relates generally to the fields of diagnostic and screening tests. More particularly, it concerns improved methods for the detection of early anti-HIV antibody in a sample, as well as early diagnostic tests to detect human immunodeficiency virus exposure or infection in infants. An additional aspect of the invention concerns methods for detecting HIV in idiopathic chronic lymphopenia patients. The invention also relates to the field of recombinant proteins, as particular recombinant proteins and recombinant protein composite preparations of several human immunodeficiency virus strains are disclosed. The invention also relates to the field of commercial diagnostic and prognostic assay plates and kits, as assay plates designed to detect an early anti-HIV antibody that include the described recombinant human immunodeficiency virus antigen or preparations of human immunodeficiency virus infected cell isolates are described.

II. Background of the Invention

Patients infected with human immunodeficiency virus (HIV) are known to eventually mount a humoral immune response to the virus. The production of anti-HIV antibody is one marker used to detect this response. In some studies, anti-HIV antibody has been reported to be more reliable for diagnosis than either HIV culture or HIV antigen detection in patient samples[1,2]. Consequently, anti-HIV antibody detection tests are the most common method of diagnosis of infection. Both EIA and Western blot assays are currently used in the detection of anti-HIV antibody.

Unfortunately, a degree of unreliability continues to exist with the use of conventional anti-HIV antibody screening methods, such as by conventional EIAs. Thus, a further confirmatory test, such as a Western Blot (WB) or fixed-cell immunofluorescence assay, have become recommended additional testing procedures.

Despite these and other additional precautionary testing measures, a number of studies report the existence of a seemingly silent period of HIV infection during which antibody to the virus is not detectable even after exhaustive testing. This period reportedly extends from the point of infection to the time infection is detectable through conventional sero-conversion assays. This silent period has been reported to persist anywhere from a few months to as much as two and one-half years before infection is detectable by conventional EIAs and Western blot assays.

While not always successful, culturing of peripheral blood lymphocytes to amplify HIV does provide for detection of the virus when anti-HIV antibody cannot be detected by conventional EIA or WB. However, several recent studies using PCR-based HIV detection methods continue to report the existence of PCR(+)positive, sero(-)negative cases in high-risk populations[10-17]. Nevertheless, PCR usually does detect infection before conventional sero-conversion methods, with the aforedescribed period of silent infection being reduced by approximately one month, at least in some cases[18].

The rate of HIV transmission in negatively tested blood, using conventional testing methods, continues to persist at a relatively constant rate[25]. For example, HIV-1 transmission from seemingly "seronegative" blood using EIA conventional methods, continue to be reported[21-23]. Donated organs also constitute a source of HIV disease transmission, with HIV infection being diagnosed in recipients of organs from individuals whom, again, test HIV seronegative by conventional assays[24].

Retrospective studies have reported that early donor education and self-exclusion measures has reduced the rate of disease transmission[26]. However, such exclusion methods together with antibody testing, while hopefully reducing the probability of at least some false negative results[27], provides only a partial and imperfect solution to the problem in at least a small subset of reported HIV cases.

Some studies report the presence of HIV specific T-cells in high risk individuals testing negative with conventional EIA, WB, and PCR based detection techniques[28,29]. Other reports have identified the existence of B-cells which produce HIV-specific antibodies in vitro that are present in EIA-negative, WB-negative, high-risk subjects[30]. While these approaches present possible alternatives, for testing, they are relatively complex and difficult procedures, and are thus impractical for large-scale clinical screening. The expense and time associated with this type of testing again leaves a need in the medical arts for a reliable and practical HIV screening and detection approach.

Early HIV infection of infants is a particularly troublesome problem. Current technology renders it difficult to diagnose whether an infant less than 18 months of age is infected, absent development of overt clinical symptoms. Conventional HIV serological tests for anti-HIV antibody are inadequate for detecting infection in an infant because the antibody detected is not necessarily that of the infant, but is that of the HIV-positive mother. This maternally derived antibody typically persists for up to 21 months in the infants system[34].

Neither IgA or IgM antibody cross the placenta. Hence, studies in children have emphasized the detection of IgA and IgM as indicators of infant HIV infection. In one study, both HIV-specific IgA and IgM were found in infants up to 12 months of age born to sero-positive mothers, with twice as many samples yielding IgA anti-HIV compared to IgM (66% vs. 33%)[35] using conventional screening assays (WB, EIA).

Currently, approximately 50% of infected infants can be identified at birth, approximately 90% by 3 months of age, and almost all by 6 months of age using combination HIV culture, PCR, IgA antibody tests, and p24 antigen tests[38]. However, the fact that HIV can be detected in only one-half of infected infants at the time of birth again points to the continued need for improved early HIV detection in infants.

SUMMARY OF THE INVENTION

The present invention, in a general and overall sense, concerns recombinant HIV envelope proteins and peptides, and early anti-HIV antibody immunoreactive fragments thereof, that are capable of immunologically binding to early anti-HIV antibodies.

As used in the description of the present invention, early anti-HIV antibodies are defined as the first anti-human immunodeficiency virus antibodies that are induced in a human infected with the HIV virus, these antibodies being capable of recognizing conformational epitopes of HIV gp160 antigen and which are not detectable by current EIA or Western Blot assay using HIV gp160 target antigen that has not have retained conformational epitopes.

The invention further provides for an improved HIV detection and screening method by allowing for the identification of early anti-HIV antibody. These early anti-HIV antibodies previously went undetected using conventional assays because the target antigens historically employed in these assays lacked sufficiently preserved conformational epitopes necessary for early antibody recognition.

The compositions and assays of the present invention comprise improved HIV target antigens that include the conformational epitopes of an HIV envelope protein, specifically the HIV gp160. The early anti-HIV antibodies detectable using the described antigen do not recognize primary sequence epitopes, and hence they go undetected with conventional serological tests that employ at least partially denatured HIV target antigen (EIA and Western blot).

Because PCR-based assays provide little improvement over conventional EIA and Western Blot serological-based assays for detecting HIV, it is expected that the presently described EIA's will also provide an improved method over PCR based detection and screening methods.

Recombinant Proteins and Peptides of Human Immunodeficiency Virus

In some embodiments of the invention, a recombinant protein comprising a recombinant human immunodeficiency virus envelope protein capable of immunologically binding an early anti-HIV antibody is provided. For example, these recombinant proteins in particular embodiments may be further defined as having a molecular weight of about 160,000 Daltons as determined by SDS/PAGE. In these particular forms, the recombinant HIV protein is an HIV envelope protein, HIV gp160.

The recombinant HIV envelope proteins of the invention may further be described by reference to the process by which they are prepared. For example, in one embodiment, the process comprises preparing a nucleic acid sequence or a restriction fragment of the human immunodeficiency virus nucleic acid sequence that encodes a human immunodeficiency virus envelope protein, such as gp160; inserting the restriction fragment into a vector capable of transfecting a eukaryotic cell to provide a recombinant vector; transfecting eukaryotic cell capable of expressing the human immunodeficiency virus envelope protein capable of binding an early anti-HIV antibody to provide a recombinant eukaryotic cell; culturing the recombinant mammalian cell under conditions suitable for expression of the recombinant HIV protein; and collecting recombinant HIV envelope protein capable of binding early anti-HIV antibody.

An example of a mammalian cell capable of expressing the HIV envelope protein nucleic acid sequence as described here is the CEM cell line. Such CEM cell lines are available through the American Type Culture Collection (ATCC). An example of the vector capable of transfecting a mammalian cell is a retroviral vector, such as pLNSX. Other carriers, such as an adenovirus or a plasmid, may also be used to transfer the HIV envelope protein encoding nucleic acid sequence. The recombinant retroviral vector in a particular embodiment of the process is the pLNSX-env.

In other embodiments of the recombinant human immunodeficiency virus protein, the protein is described as comprising a recombinant gp160 human immunodeficiency virus glycoprotein or fragments of the gp160 protein, such as the gp120 or gp41 fragment of the gp160 protein.

The recombinant HIV envelope proteins and peptides of the invention are further described in some embodiments as comprising recombinant proteins and peptides prepared from substantially purified and non-denatured lysates of mammalian cells transfected with vectors expressing recombinant human immunodeficiency virus, as well as recombinant proteins/peptides comprising the substantially purified and non-denatured expression products of these transfected mammalian cells.

In yet other embodiments, the recombinant protein/peptide preparations comprise a composite of recombinant human immunodeficiency virus gp160 proteins, the composite comprising recombinant gp160 protein from more than one human immunodeficiency virus strain.

Mammalian cell lines that are transfected with retrovirus expression vectors carrying the gp160 encoding-human immunodeficiency virus gene have been prepared with gp160-encoding nucleic acid fragments obtained from several different strains of the human immunodeficiency virus obtained from HIV-infected patients. For example, recombinant HIV envelope protein has been prepared from $HIV_{213}$ virus strain.

In a particular embodiment, the protein/peptide gp160 composite preparation comprises the recombinant gp160 protein expression product of at least three different HIV strains found to be immunoreactive with the early HIV antibody detected in a representative number of serum samples determined to be seronegative by conventional EIA and Western Blot techniques. By way of example, three such HIV strains are $HIV_{213}$, and $HIV_{AC-1}$. These HIV strains have been deposited with the American Type Culture Collection depository (12301 Park Lawn Drive, Rockville, Md. 20852). The deposit information is as follows:

$HIV_{213}$—ATCC VR 2247

$HIVAC_{AC-1}$—ATCC VR 2246

$HIV_{TP-1}$—ATCC VR 2245

Target antigen may be prepared from either the expression product obtained from eukaryotic cells transfected with retroviral or other vectors carrying these gp160 encoding nucleic acid sequences or fragments thereof, or from substantially nondenatured lysates of such transfected eukaryotic cells.

As used in the description of the present invention in the description of the human immunodeficiency virus recombinant protein/peptide preparations and cell lysates, the phrase "substantially non-denatured" in used to define a protein having a preserved configurational integrity of the human immunodeficiency virus envelope gp160 protein or a portion thereof sufficient to bind early anti-HIV antibody. Conformation of the protein/peptide used as target antigen is important in providing this early antibody recognition.

The present inventor provides here procedures that preserve sufficient conformational integrity of the protein/peptide to allow early anti-HIV binding recognition. It is anticipated that given the disclosure here, other similar protein/peptide preparation processes may be devised that result in useful target antigen compositions for early anti-human immunodeficiency virus screening. All such modified procedures, insofar as they represent minor or insignificant modification of the procedures and specific materials described herein, are therefore intended by the inventor to be embraced within the scope of the present invention.

While a number of different HIV strains were examined by the present inventor, other HIV viral strains not specifically mentioned or examined here may also be employed in the preparation of the various HIV proteins/peptides of the invention. It is expected that other HIV viral strains may be used to provide the defined substantially preserved conformational epitopically intact HIV proteins capable of early anti-HIV antibody recognition. The particularly noted HIV strains used to create recombinant protein/peptide target antigen were selected based on an observed activity to bind early anti-HIV antibody in human patient serum or plasma samples determined to be seronegative by conventional antibody testing procedures. Hence, additional such representative strains may be identified and selected using the procedures outlined herein, and subsequently processed again according to the procedures described in detail here in providing recombinant HIV antigen also useful in screening and diagnosing early anti-HIV antibody and HIV infection in a patient sample.

In a particular embodiment, the recombinant protein/peptide of the invention comprises a sufficiently conformationally intact HIV envelope protein capable of immunologically binding an early anti-HIV antibody, said antigen being isolatable as an expression product from a mammalian or other eukaryotic cell transfected with an expression vector having a sequence encoding a gp160 HIV envelope protein. The HIV gp160 envelope protein, by way of example, may be that expressed by a eukaryotic cell infected with a viral strain $HIV_C$, $HIV_{213}$, or $HIV_{AC-1}$. It is also expected that other HIV isolate strains that are capable of expressing the gp160 antigen, or instead the gp41 or gp120 HIV envelope antigen, may be used in conjunction with the present invention as well.

Purified Preparations of HIV Envelope Proteins

Further aspects of the present invention concern the purification, and in particular embodiments, the substantial purification, of the described recombinant HIV envelope protein preparations. The term "purified envelope protein" as used herein, is intended to refer to a protein composition that is isolatable from eukaryotic cells, either in the form of a solubilized population of HIV infected cells or as a protein from recombinant-expressing cells. These purified envelope proteins are further defined as essentially non-denatured and capable of binding with early anti-HIV antibody. The HIV envelope protein is purified to any degree relative to its naturally-obtainable state. In some embodiments, the purified antigen state is relative to purity of the recombinant antigen as it exists in a whole mammalian cell lysate. A purified HIV envelope protein therefore also refers to a recombinant envelope protein, free from the environment in which it may naturally occur in intact recombinant-expressing mammalian cells.

Generally, "purified" will refer to an HIV envelope protein composition wherein various non-HIV envelope components, such as other cell components, have been removed, and which composition substantially retains its antigenicity and/or capacity to interact with early anti-HIV antibody. Where the term "substantially purified" is used, this will refer to a composition in which the human immunodeficiency virus envelope protein forms the major component of the composition, such as constituting about 50%, about 60%, about 80% or about 95% of the protein in the composition or more.

Various methods for quantifying the degree of purification of the HIV protein will be known to those of skill in the art in light of the present disclosure. These include, for example, determining the activity of the preparation for detecting early anti-HIV antibody by assessing the number of different polypeptides within a fraction by SDS/PAGE analysis. In some embodiments, the recombinant HIV protein is to be purified to homogeneity expressed as an about 80% purity from a crude cell lysate so as to be identifiable in a single band of an SDS page gel stained with comassie blue. SDS page gel analysis of a protein preparation is well known to those of ordinary skill in the art.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. A specific example presented herein is the purification of recombinant gp/60 expressed mammalian cells which are solubilized using affinity binding to anti-gp41 monoclonal antibody bound to wells of plastic EIA plates.

Some of the recombinant HIV protein preparations from transfected mammalian cell lysate of the present invention have a purity of 80%. This number represents a ratio of, for example, 8 gp160 HIV antigen molecules to two non-gp160 molecules. Preparations of lower or higher purity are also useful in detecting the early anti-HIV antibody.

The preferred purification method disclosed hereinbelow contains several steps and represents the best mode presently known by the inventors to prepare a substantially purified recombinant HIV envelope protein and still maintain its native conformation. This method is currently preferred as it results in the substantial purification of the recombinant HIV protein, as assessed by SDS-PAGE determinations and ability to bind to early antibodies, while simultaneously coating EIA plates. This preferred mode of recombinant protein purification from HIV transfected mammalian cells involves the execution of certain steps in the order described hereinbelow. However, as is generally known in the art, it is believed that the order of conducting the various purification steps may be changed, or that certain steps may be omitted, and still result in a suitable method for the preparation of a substantially purified recombinant HIV envelope protein, such as the recombinant gp160 HIV envelope protein.

As mentioned above, although preferred for use in certain embodiments, there is no general requirement that the HIV transfected mammalian cell lysate always be provided in their most purified state. Indeed, it is contemplated that less substantially purified cell lysates, which are nonetheless enriched in recombinant HIV envelope protein, such as gp160 relative to the natural state, will have utility in certain embodiments. These include, for example, the detection of early anti-HIV antibody. Partially purified HIV transfected mammalian cell lysate fractions for use in such embodiments may be obtained by subjecting an HIV transfected mammalian cell lysate extract to one or a combination of the steps described herein, the HIV recombinant envelope preparations may also be obtained as a secreted product from cells carrying an HIV envelope antigen (e.g. gp160) encoding nucleic acid sequence.

Recombinant Vectors

The recombinant vectors of the invention may comprise any vehicle capable of transfecting a eukaryotic cell. By way of example, such vehicles include retrovirus vectors and adenovirus vectors. Plasmids may also be used to transfer HIV nucleic acid fragments encoding the HIV envelope proteins of the invention. In some embodiments, the retroviral vector comprises a nucleic acid sequence encoding a human immunodeficiency virus envelope protein, such as the gp160, or that encodes an early anti-HIV antibody immunoreactive fragment of the human immunodeficiency virus envelope protein.

In particular embodiments, the nucleic acid sequence encoding the human immunodeficiency virus envelope protein comprises an SalI-XhoI restriction fragment of a human immunodeficiency virus nucleic acid sequence. By way of example, the inventor has prepared SalI-XhoI restriction fragments of several human immunodeficiency viruses, particularly HIV strains C, 213 and AC-1, and blunt-end ligated the fragment into a retroviral vector, such as the pLNSX retroviral vector.

Mammalian Cell Lines

The present invention in another aspect provide recombinant mammalian cells that express the recombinant human immunodeficiency virus envelope proteins and peptides. Any variety of mammalian cells or cell lines may be used, as long as they are capable of expressing the recombinant HIV protein capable of immunologically detecting the early anti-HIV antibody. By way of example, a cell line that may be used is a CEM human cell line, particularly described as CEM human T-cells.

Methods for Preparing Recombinant HIV Envelope Protein and Peptide

Methods for preparing the recombinant HIV envelope are also provided. In one particular embodiment, the method comprises transfecting a mammalian cell with a retroviral vector genetically engineered to include a sequence encoding a human immunodeficiency viral envelope protein. These transfected mammalian cells are then subject to a screening process, such as by antibiotic resistance to G418 for example, and clones selected that express the highest amount of the human immunodeficiency virus envelope protein. By way of example, clones expressing the highest amounts of HIV envelope protein could be selected using an anti-HIV gp160 monoclonal antibody (e.g., DZ33, Medarex, Inc.).

One particular clone expressing the HIV envelope protein gp 160 isolated by the present inventors is Clone 7. Clone 7 was obtained by transfection of a CEM cell line with LNSX retroviral vector containing the env gene of $HIV_{213}$ strain. This clone 7 was examined by flow cytometry, and shown to express high levels of the recombinant HIV gp160 protein (FIG. 5).

Other clones that express a fusion protein of gp160 obtained from more than one of the HIV strains may also be obtained. Such would be achieved, for example, by constructing a retroviral vector that included a gp160 encoding fragment of nucleic acid obtained from the desired HIV isolates, and then transfecting a mammalian cell line with said construct.

Any of the herein described recombinant HIV antigens may be used alone or in combination as a target antigen for the detection of early anti-HIV antibody. Combinations of these recombinant antigens from the noted viral strains have proven to be particularly efficacious for detecting the early anti-HIV antibody in the widest range of patient samples examined to date.

Methods/Processes of Producing Recombinant HIV Envelope Protein/Peptide

The invention also provides for methods/processes of producing a recombinant HIV antigen. In one embodiment, the method comprises obtaining a nucleic acid fragment encoding a human immunodeficiency virus gp160 envelope protein; ligating the nucleic acid fragment into a vector to provide a recombinant vector; transfecting a mammalian cell with the recombinant vector to provide a transfected mammalian cell; and collecting recombinant gp160 protein. The recombinant gp160 protein may be collected by virtue of solubilizing the infected mammalian cell in a solubilizing agent that does not destroy the early anti-HIV antibody detecting capability of the antigen, such as digitonin, and then removing the cellular components in the solubilized preparation. Alternatively, the recombinant HIV antigen may be collected as a secreted product from recombinant eukaryotic cells, such as from a yeast cell that has been genetically engineered such that it secretes the gp160 HIV envelope protein.

A method that was used to collect recombinant gp160 that was used as target antigen to detect early anti-HIV antibody in a sample was through the use of 1.0% digitonin as a solubilizing agent on CEM cells infected with HIV. This procedure is described at Example 3. The recombinant HIV gp160 antigen was captured onto an ELISA plate by pouring the whole recombinant cell lysate into wells of the plate, which will be coated with mouse anti-gp41 muAB. The plate was then washed to remove cellular components and other antigens. In this fashion, the desired HIV gp160 antigen was isolated on the plate.

In a particular embodiment, the method or preparing a recombinant gp160 envelope protein comprises: obtaining a nucleic acid fragment encoding a gp160 HIV envelope protein; inserting said fragment into a vector capable of transfecting a mammalian cell; and transfecting a mammalian cell capable of expressing the gp160 envelope protein with said vector. The method may include the further step of collecting the recombinant gp160 protein.

Assay Plates

In some embodiments, the wells of the assay plates may first be coated with an anti-gp41 or anti-gp160 antibody. This would immobilize HIV gp160 antigen to the plastic in the presence of a mild solubilizing buffer, such as from about 0.1% to about 10% digitonin (particularly about 1% digitonin). Such an approach is particularly efficacious in preparing assay plates with wells made of plastic.

The assay plates in other embodiments of the invention comprise a multiplicity of microtiter wells, and in some embodiments, polystyrene microtiter wells. These wells would be coated with about 500 ng/well of the recombinant HIV envelope protein, or recombinant HIV antigen or HIV-infected whole cells or cell lysates thereof.

Early Anti-HIV Antibody Detection Assays

In yet another embodiment, the invention provides for improved anti-HIV antibody detection assays using the aforedescribed native or recombinant HIV proteins/peptides as target antigen. These improved assays, particularly ELISA sandwich-type assays, provide for the detection of early anti-HIV antibodies in sandwich-type assays, provide for detection of early anti-HIV antibody in samples that test anti-HIV antibody negative using conventional EIA and WB techniques.

The format of the EIA may be described as employing plates that are directly coated with the HIV antigen (the antigen being either recombinant HIV envelope protein expressed from HIV-transfected mammalian cells, or a lysate of substantially non-denatured, solubilized HIV-infected mammalian cells that express the HIV envelope protein), or plates that are designed to function as an antibody capture sandwich assay.

Immunoassays

As noted, it is proposed that the recombinant gp160 of the invention will find utility as immunogens, e.g., in connection with vaccine development, or as antigens in immunoassays for the detection of anti-gp160 conformational epitope-reactive antibodies. Turning first to immunoassays, in their most simple and direct sense, preferred immunoassays of the invention include the various types of enzyme linked immunosorbent assays (ELISAs) known to the art. However, it will be readily appreciated that the utility of the gp160 preparations described herein are not limited to such assays, and that other useful embodiments include RIAs and other non-enzyme linked antibody binding assays or procedures.

In some embodiments of the ELISA assay, native gp160 or appropriate peptides incorporating gp160 antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA), casein, solutions of milk powder, gelatin, PVP, superblock, or horse albumin onto the well that is known to be antigenically neutral with regard to the test antisera. This allows for blocking of nonspecific adsorption sites on the immobilizing surface and thus reduces the background caused by nonspecific binding of antisera onto the surface. Following an appropriate coating period (for example, 3 hours), the coated wells will be blocked with a suitable protein, such as bovine serum albumin (BSA), casein, solutions of milk powder, gelatin, PVP, superblock, or horse albumin, and rinsed several times (e.g., 4 or 5 times) with a suitable buffer, such as PBS. The wells of the plates may then be allowed to dry, or may instead be used while they are still wet.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 1 to 4 hours, at temperatures preferably on the order of 20° to 25° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human IgG, IgM or IgA. To provide a detecting means, the second antibody will preferably have an associated enzyme that will generate a color development upon incubating with an appropriate chromogenic substrate. Thus, for example, one will desire to contact and incubate the antisera-bound surface with a urease, alkaline phosphatase, or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethylbenzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

In each of the microtiter wells will be placed about 10 μl of the test patient sample along with about 90 μl of reaction buffer (e.g., PBS with about 1% digitonin or other mild protein solubilizing agent). Control wells of the ELISA plate will include normal sera (human sera without early anti-HIV antibody), early anti-HIV antibody collected from HIV patient subjects who had not sero-converted as assessed using Western blot, and late anti-HIV antibody obtained from patients that have seroconverted using conventional anti-HIV antibody detection techniques.

Early HIV Infection Detection in Infants

In a particular embodiment, the invention provides for a method for detecting early IgM or IgA anti-HIV antibody in a young child. These methods are improved over existing techniques, as they provide for the earlier detection of HIV infection in infants under the age of 12 months.

Early Anti-HIV Antibody Detection Kits

In yet another aspect of the invention, a kit is envisioned for early anti-HIV antibody detection. In some embodiments, the present invention contemplates a diagnostic kit for detecting early anti-HIV antibodies and human immunodeficiency virus infection. The kit comprises of reagents capable of detecting the early anti-HIV antibody immunoreactive with the native or recombinant HIV antigen described here.

In some embodiments, the kit may also comprise a container means comprising a secondary antibody capable of detecting the early anti-HIV antibody which is immunoreactive with the recombinant HIV envelope antigen.

The HIV antigen reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, plastic beads or plates, or a microscope slide. When the reagent provided is a dry powder, the powder can be reconstituted by the addition of a suitable solvent. In yet other embodiments, the kit may further comprise a container means comprising an appropriate solvent.

In some embodiments, the kit comprises a container means that includes a volume of a second antibody, such as goat anti-human IgG or IgM conjugated with alkaline phosphatase or other anti-human Ig secondary antibody, and a second container means that includes a volume of a buffer comprising a non-denaturing solubilizing agent, such as about 1% digitonin.

The kit may in other embodiments further comprise a third container means that includes an appropriate substrate, such as PNPP for alkaline phosphatase, or 9-dianisidine for peroxidase. A fourth container means that includes an appropriate "stop" buffer, such as 0.5 m NaOH, may also be included with various embodiments of the kit.

The kit may further include an instruction sheet that outlines the procedural steps of the assay, and will follow substantially the same steps as the typical EIA format known to those of skill in the art.

Idiopathic Chronic Lymphopenia Screening

In yet another aspect of the invention, methods for screening samples for evidence of HIV in idiopathic chronic lymphopenia are provided. In some embodiments, the method comprises obtaining a biological fluid sample from a patient; exposing said sample to a native or recombinant human immunodeficiency virus envelope protein which is capable of binding early anti-HIV antibodies under conditions sufficient to allow immunocomplex formation between the labeled recombinant protein and any antibody present in the patient sample, so as to provide an incubation mixture; and identifying the presence of immunocomplex formation in the incubation mixture, via some label, wherein the presence of labeled immunocomplex formation provides a screen for HIV in idiopathic chronic lymphophenia.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6. HIV 213 SalI-Bam I Sequence (nucleic acid sequence).

DETAILED DESCRIPTION OF THE PREFERRED EMBODIMENTS

Figure 1:
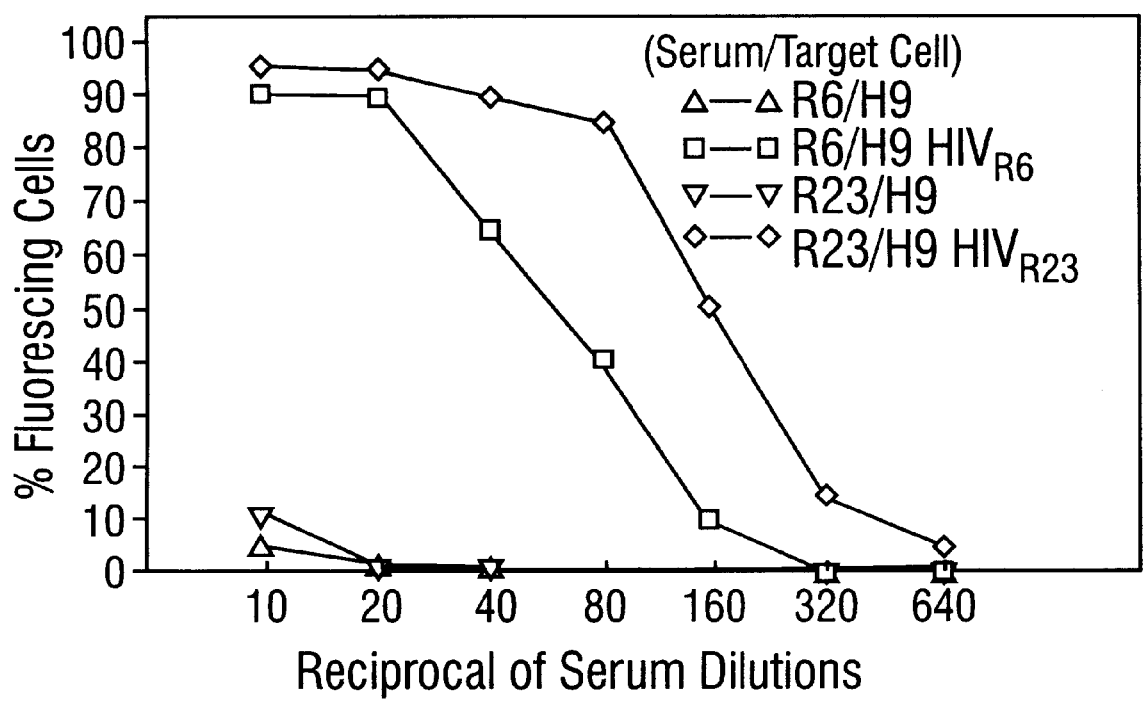
FIG. 1. Individuals testing "seronegative" by conventional EIA assay are HIV infected and have detectable early anti-HIV antibody that immuno reacts with live cells infected with viral isolates from the patient. Sera from "seronegative" HIV-infected subjects R6 and R23 were titrated on live uninfected H9 cells or H9 cells infected with their own HIV isolates ($HIV_{R6}$ or $HIV_{R23}$) and stained by FITC-conjugated goat anti-human Ig (polyvalent). The percentage of membrane-fluorescing cells were scored under a UV microscope, and demonstrates the presence of early anti-HIV antibody in the sample.

The native or recombinant HIV envelope antigen of the present invention is substantially undenatured, and has a predominantly preserved native conformation. Particular HIV strains have been identified and used in the description of some exemplary recombinant HIV target antigens herein, but are not intended to limit the scope of diagnostic/screening assays or products embraced by the claims.

An EIA that employs recombinant HIV antigens has been developed that detects the early anti-HIV antibody detected with HIV-infected live-cell immunofluorescence. The EIA of the present invention includes a target antigen in which the gp160 HIV protein expressed from vectors in mammalian cells is solubilized in such a way as to not denature it (such as by use of the solubilizing agent, digitonin), and used to coat wells of an EIA assay plate. Early anti-HIV antibody in patient sera reactive with these conformationally preserved, native antigen-mimicking epitopes will be detected using a suitable labeled anti-human immunoglobulin (such as alkaline phosphatase-labeled anti-human IgG) or, in the case of infants, anti-human IgM or IgA.

The following examples are included to demonstrate the existence in HIV-infected subjects who score negative in Western blot or current EIAs of anti-HIV antibodies that react to conformational epitopes of gp160. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Several of the methods employed in the following examples are described as follows:

Methods

Live-cell membrane immunofluorescence assays:

1. Target cells are acutely-infected H9 or CEM T-cells which are producing HIV.
2. Pipette target cell into centrifuge tubes, and spin 10 minutes at RT. Aspirate fluid, and suspend pellet in media equal to 5×volume of pellet.
3. Add 50 μl of 1° antibody to individual wells of 96-well round-bottom plates.
4. Add 10 μl of target cells to each well.
5. Seal and incubate 1 hour at room temperature.
6. Spin plate, aspirate fluid, rinse 2 times with media, and aspirate fluid.
7. Add 50 μl 2° FITC antibody, appropriately diluted, to each well, and incubate 1 hour at room temperature.
8. Spin plate (5×2,000 rpm), aspirate fluid, and rinse cells 2 times with media.

9. Add 1 drop glycerol/PBS (1:1) containing 2% formalin to each well and mix.
10. Mount cell suspension on microscope slides under cover slips.

Radioimmunoprecipitation and SDS/PAGE protocols:
Radiolabeling of cells:
1. For suspension cultures, grow cells to late log phase. Remove growth medium and wash cells one time with methionine-free culture medium. Incubate cells for 20–30 minutes at 37° C. to help deplete cellular methionine pools.
2. Remove wash medium and add a minimal volume of met-free culture medium containing 50 microcuries/ml of $^{35}$S-methionine. Incubate for 3–4 hours, or as required.
3. To harvest cells, collect suspension cultures by centrifugation and wash one time with cold PBS. Add 1.0 ml of lysing buffer (0.5% NP40, or 1% digitonin, etc.). Transfer to a microfuge tube, vortex and hold sample at −70° C.
4. Determine amount of radiolabeled protein using TCA precipitation. Just before protein analysis, centrifuge sample for 15 minutes in a microfuge to pellet nucleic acids and insoluble debris.

Immunoprecipitation from cell lysates and SDS/PAGE:
1. Aliquot an appropriate volume of lysate into a screw-cap microfuge tube based upon the amount of radiolabeled protein. A typical RIP might contain $10^6$ cpm. If preclearing is required, add 1:100 (v) antibody (normal serum), vortex and incubate on ice for 30 minutes. Add 100 microliters of either Protein A-Sepharose or formalin-fixed Staphylococcus aureus (Cowan strain) to sample, mix and hold on ice for 30 minutes. Centrifuge for 5 minutes and recover supernatant and transfer to new screw-cap tube.*
Samples (1–2×10$^6$ cell equivalents) of precleared lysate are immunoprecipitated with 3–5 μl of sera or 100 μl of tissue culture monoclonal antibody supernatant overnight at 4° C. Precipitates are recovered with S. aureus and analyzed by SDS (10%)-PAGE under reducing conditions (5% 2-mercaptoethanol).

EXAMPLE 1

Early Anti-HIV Antibody with Live-Cell Immunofluorescence as Target Antigen

The present example demonstrates the presence of early anti-HIV antibodies in the sera of human patients previously diagnosed as being seronegative by conventional anti-HIV antibody detection techniques.

The presence of early anti-HIV antibodies in 4 of 4 high-risk infected EIA-, WB-individuals was shown in the present example using a nondenaturing test (live-cell membrane immunofluorescence). These anti-HIV antibodies were of the IgG isotype, and were found to react with their homologous HIV, as well as with a number of other HIV-1 isolates (Table 1).

TABLE 1

Seronegative" Patients Possess Antibody Reactive to Multiple HIV-1 Isolates:
Summary of Serum Antibody Titers Against HIV-Infected Cells

| | Reciprocal of serum dilution that stained 50% of cells H9 infected with | | | | | | | |
|---|---|---|---|---|---|---|---|---|
| Serum | Uninfected H9 | HIV$_{R6}$ | HIV$_{R23}$ | HIV$_{R58}$ | HIV$_{pm213}$ | HIV$_{G1}$ | HIV$_{AC-1}$ | HIV-III$_B$ |
| R6 | <10 | 60 | 60 | 10 | 40 | 20 | 50 | <10 |
| R23 | <10 | 160 | 160 | 20 | 160 | 640 | 320 | 20 |
| R78 | <10 | 30 | 70 | 60 | 15 | 50 | <10 | 40 |
| R82* | <10 | 70 | 15 | 30 | 80 | ND | 15 | ND |
| R58 | <10 | 320 | <10 | 100 | 1000 | 200 | 1000 | 640 |

Note:
ND, Not Determined
*This serum was preabsorbed with uninfected H9 cells to remove antibodies that reacted with H9 cells.
R58 is a EIA+, WB+ HIV-infected subject for comparison.

These sera did not react with HIV-uninfected cells, as controls.

EXAMPLE 2

Immunoreactivity of HIV Strains in Clinical Screens

The present example presents a survey of different HIV strains, as the present inventors' earlier studies showed that EIA+, WB+ sera from HIV-infected individuals possessed a great deal of type-specificity for native HIV envelope antigens, and are active for different HIV strains when using live-cell immunofluorescence. Table 2 provides data demonstrating that certain HIV strains appear to be recognized by antibodies from more infected individuals than other HIV isolates.

TABLE 2

Reactivity of Sera from HIV EIA/WB (+) Individuals for env Antigens Expressed on H9 Cells Infected with Different HIV Isolates.

| SERA | H9 | AC-1 | CP-1 | MCK | 0 | 214 | III$_B$ | 205 | HTLV-III$_B$ | TP-1 | AK-1 | SK-1 | 213 | G1 |
|---|---|---|---|---|---|---|---|---|---|---|---|---|---|---|
| Control | — | — | — | — | 10 | — | — | — | — | — | — | — | — | — |
| Pt. 11 | — | 20* | — | — | — | — | 80 | 20 | — | — | — | — | 20 | — |
| 1 | — | 5120 | 80 | 40 | — | — | 40 | 80 | 2560 | 2560 | 320 | 20 | 2560 | 1280 |
| K | — | 40 | — | — | 160 | 160 | — | 5120 | 160 | 1280 | — | 20 | 2560 | — |
| 8 | — | 5120 | 20 | — | 20 | — | 20 | 40 | 5120 | 2560 | 160 | — | 5120 | 40 |
| 12 | — | 160 | — | — | 40 | — | — | — | — | 320 | — | — | — | — |
| 5 | — | 160 | 80 | 80 | 40 | — | 160 | 160 | 5120 | 640 | 320 | — | 5120 | 160 |
| 2 | — | 5120 | 80 | 320 | 160 | — | 40 | 1280 | 160 | 1280 | 2560 | 20 | 640 | 640 |
| 10 | — | 2560 | — | 80 | 160 | 10 | 40 | 40 | 5120 | 320 | 5120 | 160 | 5120 | 80 |
| 6 | — | 2560 | — | — | 20 | — | 320 | 80 | 1280 | 320 | — | — | 1280 | — |
| 13 | — | 5120 | — | — | — | 10 | 80 | 160 | 5120 | 2560 | 160 | — | 5120 | 80 |
| 15 | — | 160 | — | — | — | — | 160 | — | 640 | 2560 | 40 | — | 5120 | 40 |
| 20 | — | 5120 | 20 | — | — | — | — | — | 2560 | 166 | 2160 | 160 | 5120 | 20 |
| 17 | — | 5120 | 40 | 20 | 80 | 2560 | 20 | 320 | 160 | 5120 | 1280 | 320 | 1280 | 640 |
| 18 | — | 2560 | — | 20 | 160 | 5120 | — | 160 | 160 | 1280 | 320 | 320 | 2560 | 160 |
| 21 | — | 1280 | — | 1280 | 640 | 1280 | — | — | 2560 | 2560 | 160 | 320 | 1280 | — |
| 9 | — | 1280 | — | — | — | 5120 | 40 | 5120 | 640 | — | 1280 | 10 | 2560 | — |
| 14 | — | 2560 | 10 | 20 | 20 | 160 | 20 | 1280 | 640 | 5120 | 5120 | 1280 | 2560 | 2560 |
| 16 | — | 1280 | — | 40 | 40 | 2560 | 160 | 2560 | 5120 | 1280 | 1280 | 80 | >640 | 80 |

*Data expressed as reciprocal of serum dilution that stains 50% of cells in live-cell immunofluorescence assays.

Other comparisons have been run using "early" sera from infected high-risk individuals (EIA-negative, WB-negative). These data are summarized in Table 3 which shows that HIV strains 213, AC-1 and C react with most of the sera.

TABLE 3

Live-Cell Immunofluorescence Reactivity of "Early" Antibodies for Different HIV-1 Strains

| Total # of Patients tested | Number of Positive * for These Target Cells | | | | | | |
|---|---|---|---|---|---|---|---|
| | H9 | H9+ MN | H9+ RF | H9+ 111$_B$ | H9+ 213 | H9+ AC-1 | H9+ C |
| 13 | 0 | 0 | 2 (40, 80) | 2 (40, 80) | 11 (40–160) | 10 (40–80) | 12 (40–160) |

Positive = ≧40
() = Range of titers. Titer is reciprocal of serum dilution that stains 50% of the cells.

Cumulatively, all of the data for both advanced infected as well as the "early" infected subjects indicated that one or more of these three HIV strains will react with antibodies from nearly all, if not all, infected people.

A larger group of high-risk EIA-negative, WB-negative individuals has also been tested. It was found that antibodies reactive in live-cell membrane immunofluorescence were present in about 25% of them. Data in Table 4 show the anti-HIV immunofluorescence titers from the single high-risk patient who comprised the study reported in Clerici et al[28].

TABLE 4

Membrane Immunofluorescence Titers of Sequentially obtained sera samples from Same Patient

| | Target Cells | |
|---|---|---|
| Serum | H9 | H9-HIV |
| Visit #8 | — | 30* |
| Visit #10 | — | 50 |
| Visit #15 | — | 70 |

*Reciprocal of serum dilution that stained 50% of cells.

This individual possessed low but significant anti-HIV antibody titers by membrane fluorescence, even though he was "sero-negative" in the FDA-approved serological tests, and was PCR-negative for HIV[28]. Correspondingly, he possessed HIV-reactive T-cells, which formed the basis of their report.

Table 5 shows the membrane fluorescence titers for another series of individuals. The coded samples included a number of normal controls, as well as infected individuals who were sero-positive by the routine tests.

TABLE 5

Summary of Membrane Immunofluorescence Reactivity of Sera

| | | Number Positive on These Target Cells | | |
|---|---|---|---|---|
| Risk Group | # of Patients | H9 | H9-HIV$_{213}$ | H9-HIV$_{AC-1}$ |
| Heterosexual Low Risk | 10 | 0 | 0 | 0 |
| HIV-Infected EIA/WB-pos. | 10 | 0 | 10 | 10 |
| Homosexual High Risk (EIA−, WB−) | 5 | 0 | 1 | 3 |

Positive = Titer ≧ than 1:40

The membrane fluorescence titers corresponded perfectly with those tests. This group also included five high-risk individuals who were sequentially bled over a period of eight to ten months. One of these individuals (20664) had a low immunofluorescence titer to $HIV_{213}$ on the first visit, which was at a time that he was still sero-negative by the FDA-approved tests. By approximately four months later, this individual was positive in EIA and Western blot and had a titer of 1:160 by membrane immunofluorescence to $HIV_{213}$, but also to $HIV_{AC-1}$. The second individual (40301) developed a titer by membrane immunofluorescence to $HIV_{AC-1}$ on his second visit, which increased by the next visit. A third subject (41593) became sero-positive in the membrane immunofluorescence test on his last visit, but he was negative by EIA and Western blot. The other two individuals in the group were high-risk individuals who never sero-converted by the conventional tests, and never sero-converted by membrane immunofluorescence.

Table 6 summarizes the membrane immunofluorescence reactivities for 65 individuals. The groups comprised normal controls, positive controls (EIA/Western blot positive), and 36 individuals who were high-risk, but sero-negative by EIA and WB. 12 of the latter were positive by membrane immunofluorescence, and had already been found to also possess T-cells reactive to HIV peptides.

TABLE 6

Membrane Immunofluorescence Titers of Sera

| Risk Group | # of Patients | No. w/HIV Reactive T-Cells | No. Membrane Immunofluorescence Positive with These Target Cells | | |
|---|---|---|---|---|---|
| | | | H9 | H9-213 | H9-AC-1 |
| Low Risk Control | 18 | 0 | 0 | 0 | 0 |
| HIV-Infected EIA+, WB+ | 11 | ND | 0 | 10 | 11 |
| High Risk EIA−, WB− | 36 | 11 | 0 | 10 | 12 |

ND = Not Determined
Positive = Titer ≧ 40

The data from all of the high-risk "seronegative" subjects are summarized in Table 7. Most of these sera were obtained only once and includes an additional 50 patient sera.

TABLE 7

Summary of Live-Cell Immunofluorescence Testing of Sera from High-Risk Subjects for Antibodies to HIV

| Subject Group | # of Subjects | # pos | Range of Titers |
|---|---|---|---|
| High-risk Sero-neg. by WB/EIA | 109 | 29 | 20–130 |
| Low-risk controls | 50 | 0 | — |
| AIDS Patients | 83 | 83 | 100–5000 |

29 of 109 subjects possessed antibodies reactive to live-cell florescence to at least one of the three HIV strains, eight of these were randomly examined for immunoprecipitation of digitonin solubilized viral protein in infected cells and found that they all reacted with HIV gp160. In live-cell fluorescence, low-risk HIV-NEGATIVE individuals have not been found positive (i.e., titer≦1:10), and titers in infected subjects largely correspond to the stages of disease. High titers in live-cell fluorescence were usually found in individuals who also scored positive in EIA and Western blot, and lower titered individuals usually did not score in EIA and Western blot.

Relative Sensitivity of Live-Cell Immunofluorescence Assay

Live-cell immunofluorescence is not necessarily a more sensitive assay than EIA and WB on all occasions. Control (negative) sera do not stain cells at dilutions greater than 1:10 but do give positive reactions at such low dilutions in EIA and WB. Often control sera need to be diluted to ≈1:100 to be unreactive in EIA and WB, and it is likely that the high sensitivity of these tests allows scoring of the very low amounts of antibodies present in human sera which react with most antigens. About 44–95% of HIV-infected individuals possess significant levels of auto-antibodies[33]. Live-cell fluorescence is too insensitive to detect these antibodies in sera diluted beyond 1:10. Also, sera positive for anti-HIV antibodies can be diluted out to 1:10,000–1:30,000 and remain reactive in EIA and WB, whereas these same sera are unreactive in live-cell fluorescence when diluted beyond 1:5000. Using live-infected cells allows detection of antibodies to native conformational epitopes, not greater sensitivity of detection of antibodies on a molar basis.

EXAMPLE 3

Solubilization Studies—Non-Live Cell Target Antigen for Detecting Early Anti-HIV Antibody The present example demonstrates the utility of non-live cell target antigen for detecting the early anti-HIV antibody in a patient sample. The data here also demonstrates the importance of substantially preserved conformational epitopes of the human immunodeficiency virus envelope protein for detecting the early anti-HIV antibody.

The effects of different solubilizing agents on HIV protein immunoreactivity for early anti-HIV antibody was examined by preparing HIV target antigen with a number of different detergents. This study demonstrates that early anti-HIV antibodies may be detected in human serum samples using other than live cells infected with HIV as target antigen, these samples having previously been determined to be seronegative for antibody using denatured HIV protein as target antigen (in Western blot and conventional EIAs).

HIV-infected human CEM cells were solubilized with one of the agents listed in Table 8. Each antigen preparation was tested for ability to be immunoprecipitated by early anti-HIV antibody contained in sera from six patients. These patient sera tested positive for early anti-HIV antibody using the live-cell immunofluorescence assay, and negative for the presence of anti-HIV antibody by conventional Western Blot assay with denatured HIV target antigen. Each antigen preparation was also tested with a control serum sample that did not contain early anti-HIV antibody, as determined with the live-cell immunofluoresce assay ("NS"=normal sera).

Table 8 summarizes all the data and shows that digitonin is a representative solubilizing agent that may be used to provide the least denaturing effect on the protein/peptide for use as a target antigen as compared to the other detergents examined in this study. These data provide evidence that these "early" antibodies recognize conformational epitopes of HIV gp160. It is contemplated that digitonin at concentrations of between about 0.1% to about 5% may be used to prepare the target HIV antigen of the present invention without loss of early anti-HIV antibody detecting reactivity.

TABLE 8

Summary of RIP/SDS-PAGE Examination of Reactivity of "Early" Antibodies to HIV gp160 Solubilized in Various Detergents

| Detergent | "Early" Antibody* Immunoprecipitation |
|---|---|
| 0.5% SDS | — |
| 0.5% NP40 (nonylphenoxy polyethoxy ethanol) | 3 sera pos; 3 sera neg |
| 10 mM CHAPS | — |
| 0.5% Deoxycholate | — |
| 1.0% Octylglucoside | — |
| 1.0% Digitonin | + (all 6) |
| 1M $K_2PO_4$ | — |
| 0.5 mM Dodecylmaltoside | — |
| 0.3 mM Theirst | — |

*6 different sera tested. All were WB-negative but positive in live-cell immunofluorescence on HIV-infected cells.

Figure 4:
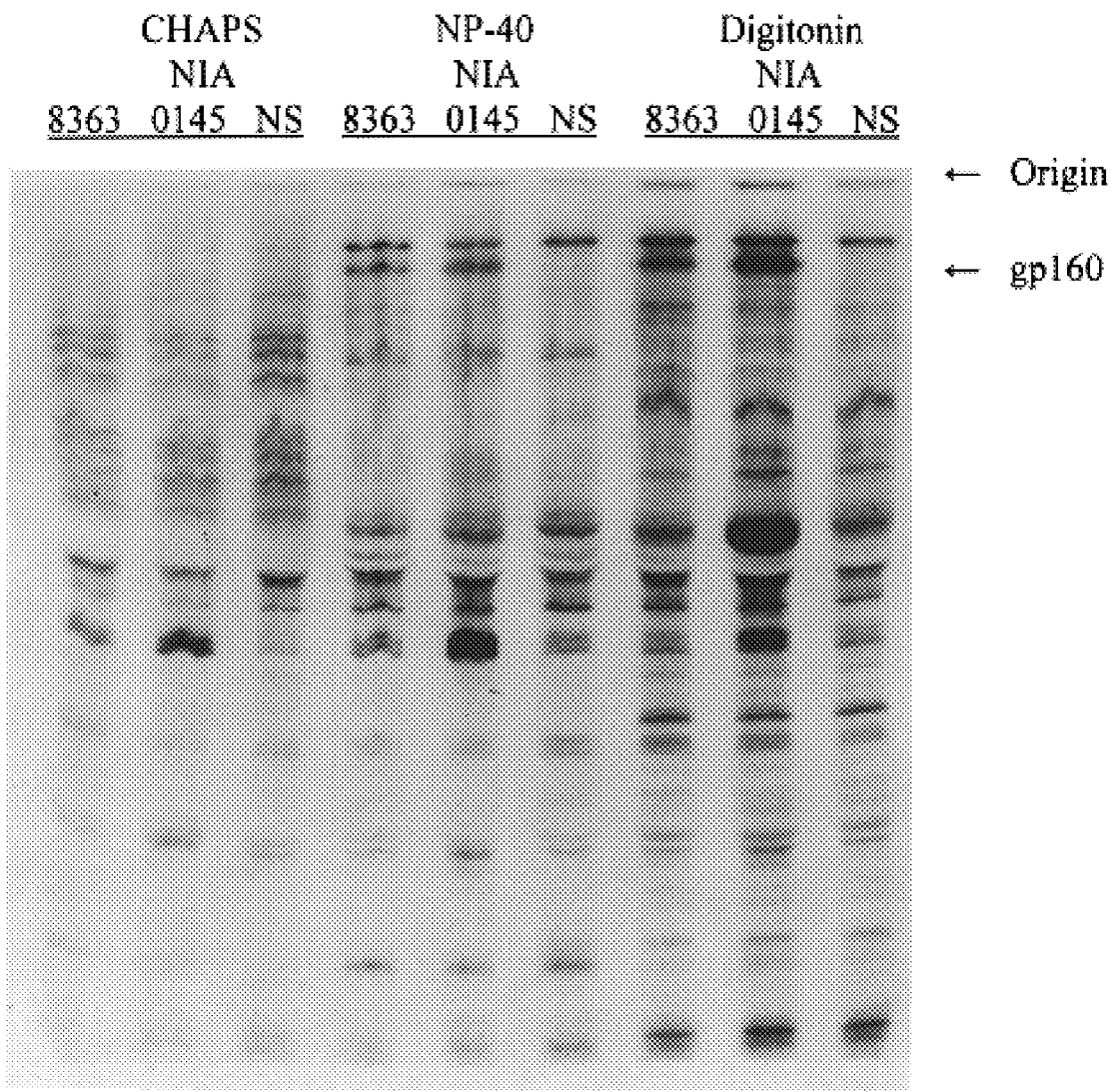
FIG. 4. SDS/PAGE of [$^{35}$S] methionine-labeled H9 cells infected with HIV lysed in different detergents, and immunoprecipitated with either normal human serum (NS) or serum from patients with early anti-HIV antibodies (NIA-0145, 8363).
Figure 5A:
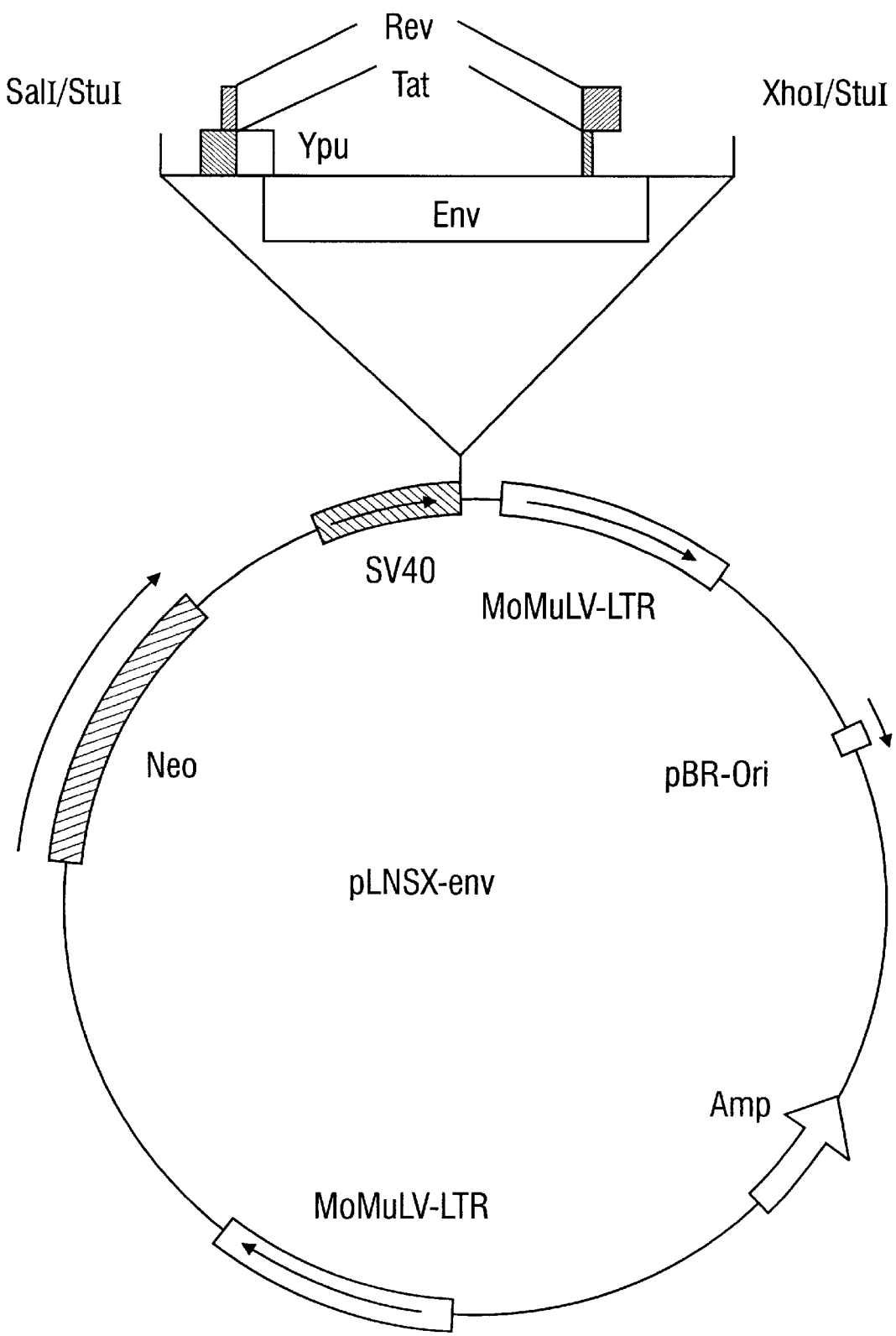
FIG. 5. Flow cytometry was used to determine the levels of anti-gp41 and anti-gp120 mAb bound to three independent clones of $HIV_{213}$ gp160-transfected cells (CEM-HIV env-1, env-4, env-7) compared to non-expressing controls. Cells were stained with 20 μg/ml of control (irrelevant IgG, shaded curve) or anti-g41 mAb (5F3 human mAb, dashed line) or anti-gp120 ($gpIII_{2,3}$ murine mAb, solid line). Detection was done using a second species-specific phycoerytherin (PE)-conjugated antibody.
Figure 5B:
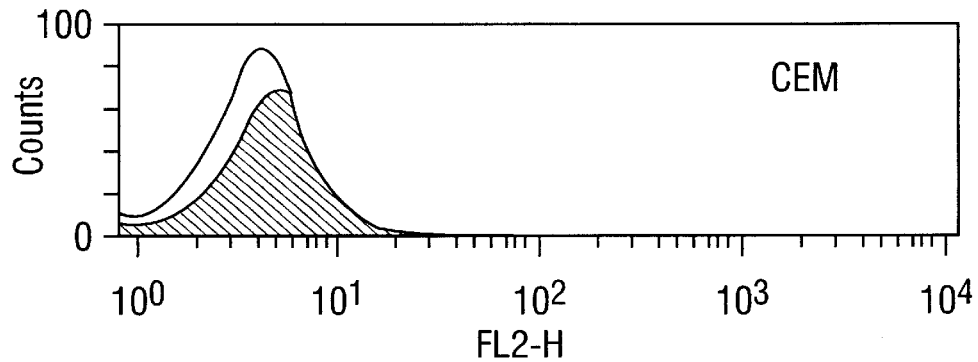
Figure 5C:
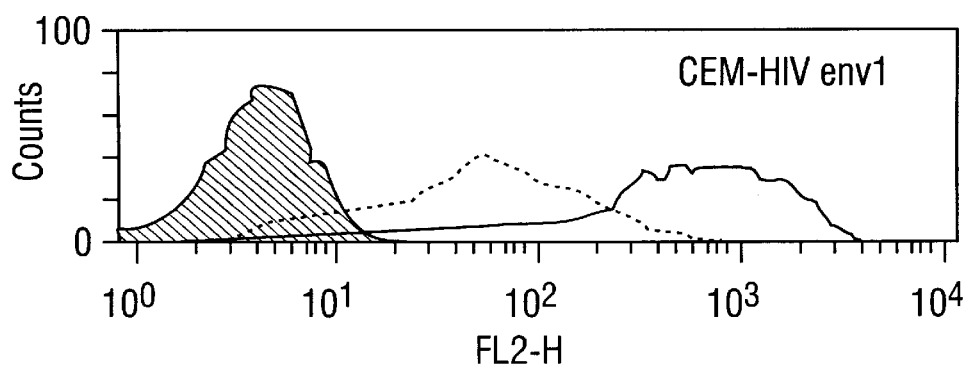
Figure 5D:
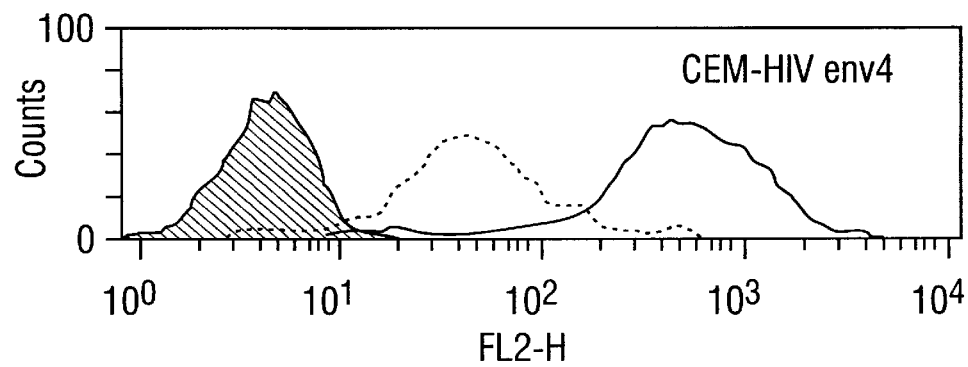
Figure 5E:
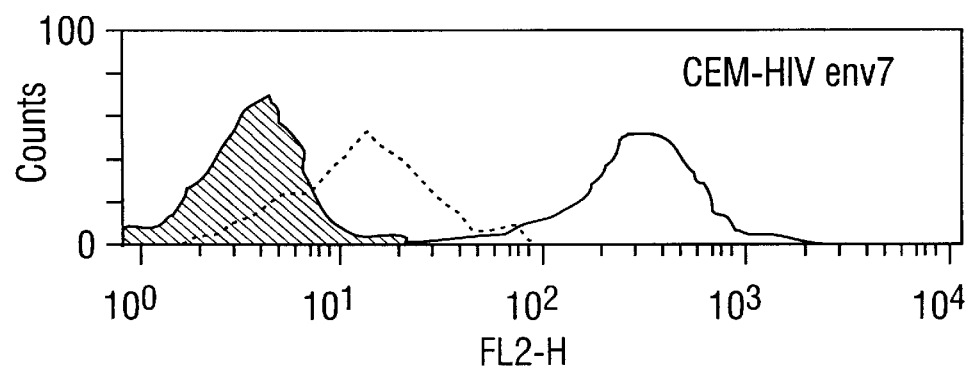

FIG. 4 shows representative examples of this work and demonstrates that "early" antibodies immunoprecipitated gp160 solubilized in about 1% digitonin and 0.5% NP40. Early anti-HIV antibody was detected in all sera samples where gp160 solubilized in digitonin was used as target antigen. Early anti-HIV antibody was also detected in three out of the six patient sera samples using the NP40 solubilized HIV target antigens. However, early anti-HIV antibodies were was not detected in any of the sera using HIV antigens treated with 10 mM CHAPS, 0.5% SDS, 0.5% deoxycholate, 1.0% octylglucoside, 1 mM $K_2PO_4$, 0.5 mM dodecylmaltoside or 0.3 mM Theirst.

In one embodiment, HIV-infected cells will be solubilized in 1% digitonin, and used to coat EIA plates as the target antigen.

Figure 2:
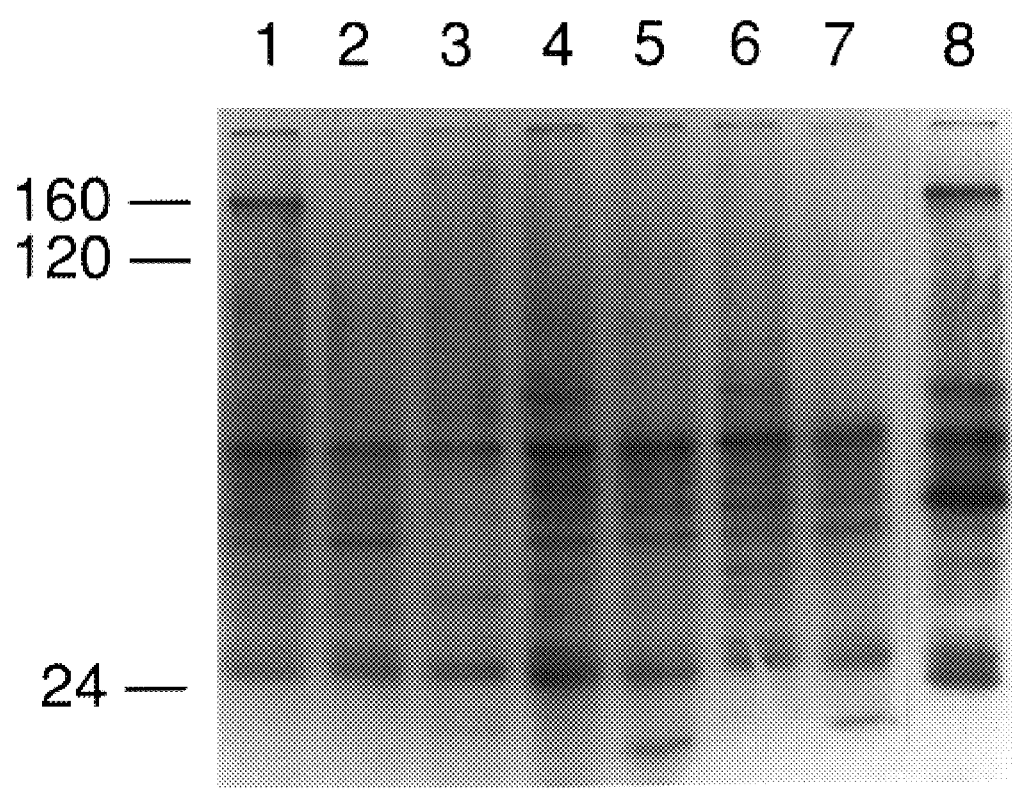
FIG. 2. Antibody from "seronegative", yet HIV-infected subject reacts with HIV gp160 of HIV-infected cell lysates. SDS-PAGE analysis of immunoprecipitates from NP-40 solubilized [$^{35}$S] methionine-labeled H9 cells (uninfected or infected with $HIV_{pm213}$). Lanes 1–3 and 8 are lysates from H9 infected with $HIV_{pm213}$ and lanes 4–7 are uninfected H9 lysates. Lanes 1 and 4, R23 serum; lanes 2 and 5, R6 serum; lanes 3 and 6, R78 serum; lanes 7 and 8, R58 serum (R23, R6, snf R78 are negative in routine EIA and Western blot, for HIV antigens, R58 is EIA and WBt).

These radioimmunoprecipitations (RIP) and SDS/PAGE studies also demonstrated that the antibodies were reacting to viral antigens, and not viral-induced cellular antigens. The HIV antigens solubilized with CHAPS did not reveal a detectable immunoprecipitate with early anti-HIV antibody containing sera (FIG. 2, lanes 1 and 2). One of the four sera provided an immunoprecipitate using 0.5% NP40-solubilized $^{35}$S-methionine labeled infected cells (FIG. 2, lane 4 and 5). Slight denaturation by this percentage NP40-solubilizing agent destroyed the antigenic epitopes recognized by the antibodies in the other 3 sera.

Figure 3:
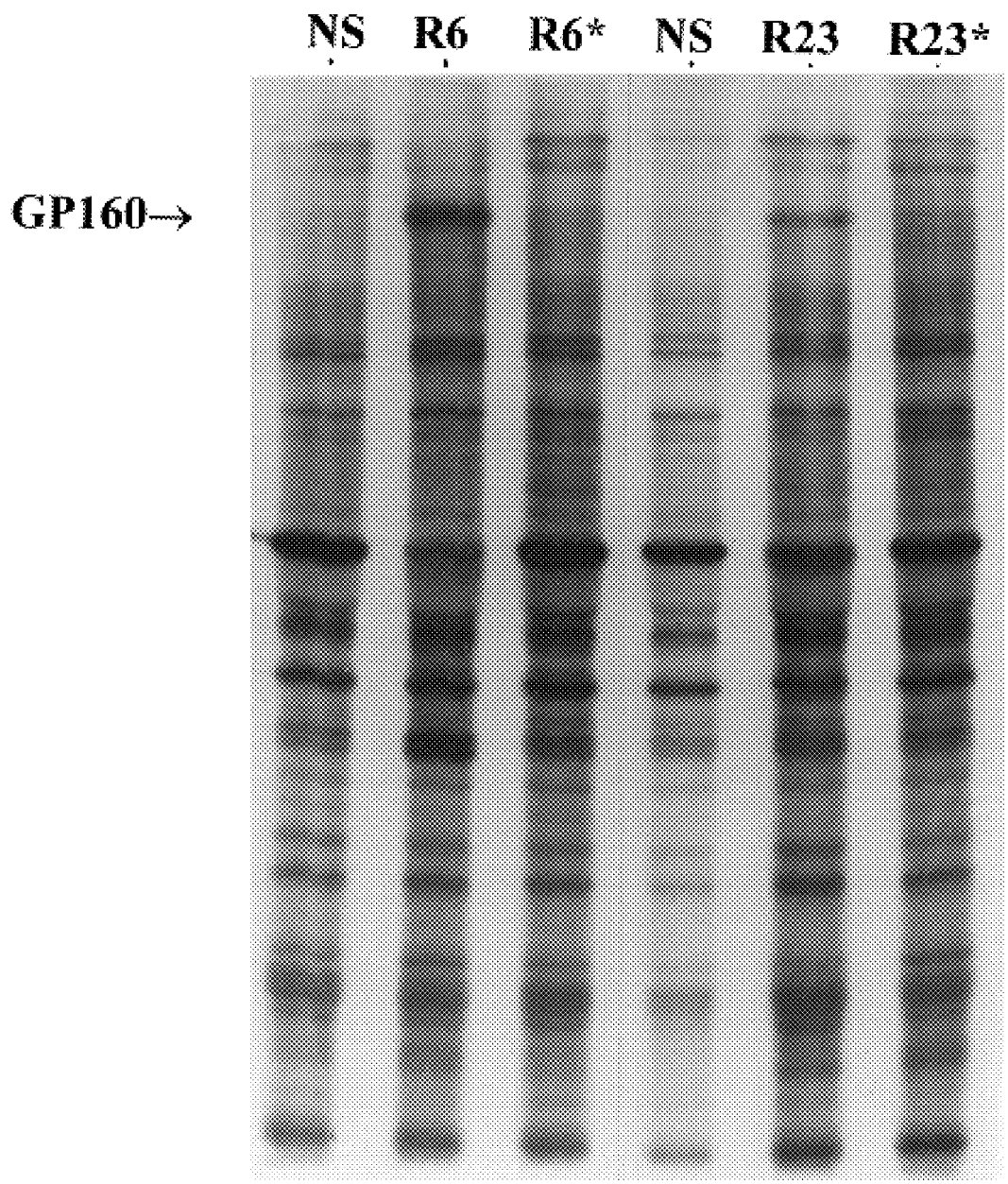
FIG. 3. RIP of digitonin-lysed H9 cells infected with $HIV_{213}$. NS=normal human serum; R6 and R23="early" serum; *=lysate precleared with anti-gp160 monoclonal antibody (F105).

The one reactive sera immuno-precipitated a protein of about 160,000 molecular weight, FIG. 2). The protein that was immunoprecipitated was confirmed to be HIV gp160 by showing that such RIP reactivity could be eliminated by precleaning the NP40-cellular lysate with anti-gp160 monoclonal antibody (FIG. 3).

The following examples outline: (a) development of CEM lines expressing gp160 from HIV strains AC-1 and C; (b) format of the EIA (i.e., direct coating of the wells with antigen or antibody-capture sandwich assay), including the determination of appropriate blocking reagents to reduce background binding in the EIA; determination studies on the EIA plates in a dry or wet use format, and how to preserve the HIV protein antigenic conformation on the assay plate in commercial embodiment of the invention.

EXAMPLE 4

Recombinant gp160 HIV Proteins/Peptides

The present example demonstrates the utility of the invention for providing conformationally intact recombinant target antigen that is capable of immunologically reacting with early anti-HIV antibody. The presence of the early anti-HIV antibody is comparable to the anti-HIV antibody detection observed with the live-cell immunofluorescence assay.

Stable expression of the SalI-XhoI restriction fragment from HIV strain 213 in a retrovirus vector (PLNSX) in CEM human T-cells has already been achieved (FIG. 5). This fragment was blunt-end ligated into the vector, and following transfection by electroporation, the cells were selected with G418, and then individual clones were obtained by limiting dilution and tested for high expression of envelope using F105 monoclonal antibody Medarex, Inc. to HIV gp160. The resulting clone (Clone 7) was studied by flow cytometry (FIG. 5) and shown to highly express gp160.

The Clone 7 was useful in live-cell fluorescence assays and has been observed to react with the early anti-HIV antibodies detected using H9 HIV infected cells. Cloning of the envelope genes of the other two HIV strains, $HIV_C$ and $HIV_{AC-1}$, has also been accomplished using the expression vector system described above.

Further evidence demonstrating the importance of preserved conformational integrity of HIV target antigen for early anti-HIV antibody binding and detection is provided in the studies conducted by the inventor using a recombinant gp160 HIV antigen. The envelope of $HIV_{213}$ was expressed in E. coli. This antigen was then used to attempt immunoprecipitation of early anti-HIV antibody from patient sera identified as having early anti-HIV antibody in the live-cell immunofluorescence assay.

The recombinant gp160 HIV envelope antigen expressed by E.coli was not precipitated by the early anti-HIV antibodies in the patient sample, while the digitonin solubilized $HIV_{213}$ infected cell antigen did. These results demonstrated that early anti-HIV antibody is unable to immunologically bind gp 160 HIV surface antigen having only a preserved primary structure, as E.coli is not capable of providing a recombinant protein having sufficient conformational characteristics necessary for recognition by the early anti-HIV antibody. The over expression of gp160 in bacteria does not allow for proper folding and glycosylation of the protein.

EXAMPLE 5

Detection of Anti-HIV Antibody in Infants

The present examples demonstrates the existence of early anti-HIV antibody in infants, and thus the utility of native recombinant HIV antigen assays for detecting HIV infection in infants.

Samples examined in these studies were obtained from a pediatric HIV population made up from samples from 48 babies (ages 1 day to 6 mos) born from mothers determined to be HIV sero-positive using conventional antibody detection techniques. PBMCs were also cultured for HIV detection by p24 antigen-capture EIA and PCR. HIV was found in six of these infants.

Table 9 summarizes the results of titrations of the infant sera in live-cell membrane immunofluorescence against uninfected and infected cells.

TABLE 9

Live-cell immunofluorescence testing of infant
sera for IgM reacting with HIV

| Subject Group | No. | No. Positive for HIV by PCR* | No. Positive for IgM to HIV (Titers) | No. Positive for IgM to Uninf. Cells |
|---|---|---|---|---|
| Infants born to HIV+ mothers (ages 1 day–6 mos) | 48 | 6 | 6 (10–80) | 0 |
| Control Infants (ages 1 day–5 mos) | 13 | 0 | 0 | 0 |

*PCR amplification of LTR-gag sequences in cultured PBMC

Each of the six infected infants possessed early IgM antibody that reacted to HIV-infected cells. The sera did not react with uninfected cells, and these sera were also reactive after elimination of the IgG by absorption with Sepharose protein G, to eliminate the possibility that rheumatoid factor was being detected. The uninfected infants did not possess anti-HIV IgM, so there was a 100% concordance between the presence of IgM to HIV by live-cell fluorescence and the presence of virus. Noteworthy was the presence of a moderate titer of anti-HIV IgM in the plasma obtained from a one-day-old baby who was found to be infected. The data provides a positive indication that the baby was obviously infected in utero.

These data show that infected infants possess HIV-specific IgM which can be detected using live-infected cells as antigen. A pediatric HIV-testing kit which will detect IgM and IgA antibody reactive with conformational epitopes of HIV proteins is thus provided for this particular application.

The data supports the contention that HIV-specific T-cells, B-cells, and anti-HIV antibodies which recognize conformational epitopes are produced during the early windows of otherwise immunologically silent infection, and eventually infected individuals produce antibodies which react to denatured proteins (conventional "sero-conversion" in current EIA/WB assays).

A prospective study by other investigations of infants born to HIV sero-positive mothers shows that out of 12 HIV culture-positive infants, 10 had IgA antibody against HIV recombinant protein detectable from birth to twenty-seven weeks of age[36]. In most cases, the first sera tested were collected after two months of age. Among children older than one year, all samples were positive for HIV-specific IgA, while only 50% contained detectable IgM. Notably, only two of thirteen infected infants under 3 months of age had IgA detected by their modified Western blot procedure. Regardless of the testing procedure (Western blot or dot blot) the first serum sample with detectable antibody to HIV was reactive to envelope glycoprotein gp160.

The above findings demonstrate the utility of the present invention as a new diagnostic test for HIV in infants, that is improved over current methods as it detects HIV much sooner than standard screening methods, and is further specific for infection of the infant, and not the mother.

The present invention in particular embodiments comprises a testing regimen whereby the pediatric subjects may be screened for HIV infection through early anti-HIV antibody testing via presence of specific IgM or IgA to conformational epitopes of HIV gp160, as part of an improved early diagnosis of pediatric HIV-infection.

EXAMPLE 6

Screening Methods for Blood in Blood Banks

The current tests for HIV infection do not score individuals who have been recently infected, and even miss a small fraction late in the pre-AIDS period. Since virus may be detected from such EIA-negative, WB-negative patients, they would very likely be able to transmit the virus to other people during that time. Further, if they donate blood believing that they are not infected, danger to a transfusion recipient of their blood exists. Hence, one of the greatest needs for the present types of test will be extended use in blood bank monitoring of donated blood. In addition, since many of these types of subjects are most likely sexually active, the presently disclosed tests have utility for detecting early HIV-1 infected individuals who are tested in clinics dealing with sexually transmitted disease, alternative test sites, etc.

The present methods provide for the use of recombinant, a non-live cell HIV target antigen that detects the early anti-HIV antibody. The methods in some embodiments comprise an EIA in which gp160 expressed from vectors in mammalian cells will be solubilized, such as in digitonin, and used to coat wells of a standard EIA plate. Then, early anti-HIV antibody in patient sera which react with these native antigens will be detected using a labeling agent, such as alkaline phosphatase conjugated to anti-human Ig antibody.

EXAMPLE 7

EIA Assay with Nondenatured, Recombinant GP160 HIV Antigen

The present example demonstrates the utility of the invention for providing an EIA for the detection of early anti-HIV antibodies employing a non-denatured, non-live cell HIV target antigen. These non-denatured HIV antigens present a reduced biohazard relative to the HIV infected cell used as target antigen, while providing essentially the same anti-HIV early antibody detection activity. The particular nondenatured, non-live cell HIV target antigen illustrated in the present example is a recombinant gp160 HIV antigen.

While the test will provide for the detection of early anti-HIV antibody, it will also demonstrate a positive reaction with late antibodies detected with conventional anti-HIV antibody detection methods.

The gp160 HIV target antigen will be prepared as described in Example 4 ($HIV_{213}$). However, any HIV envelope protein that may be isolated as part of an encoding nucleic acid sequence and recombinantly produced may be used in conjunction with the present invention, said antigens having the preserved conformational integrity necessary to facilitate recognition and binding of the early anti-HIV antibody. In one example, the gp160 expressed from vectors in mammalian cells will be solubilized in about 1% digitonin and used to coat, for example, the wells of a standard 96-well microtiter plate.

Any early anti-HIV antibody present in a sample, preferably a biological sample (solid tissue or fluid) will immunologically react with the antigen, and the early antibody being detected using alkaline phosphatase-labeled anti-human IgG or, in the case of infants, anti-human IgM or IgA.

The EIA assay may follow any variety of testing formats known to those of skill in the art, given the information of the present disclosure, such as the direct coating of assay wells with antigen or antibody-capture sandwich assay. It is anticipated that the assay plates that contain or are treated with the antigen may be dried without significant loss of capacity for binding or attracting the binding of early-anti-HIV antibody.

Determination of EIA Format

HIV gp160-expressing cells which react to all "early," as well as "late," antibodies will be solubilized in a mild solubilizing agent, such as digitonin. This lysate will be size-fractionated on Sephadex G2000 columns in the cold, and the peak containing HIV gp160 (as determined by RIP) will be used to coat polystyrene microtiter wells at 500 ng/well. Following 3 hrs of coating, the wells will be "blocked" with BSA, and rinsed 5 times with buffer. The wells will be either allowed to dry or left wet in PBS. 10 μl of "early" antibody will be added to individual wells containing 90 μl of reaction buffer (PBS containing about 1% digitonin). The following steps will be typical EIA format involving incubation for about 1 hour at room temperature, 3 rinses with about 1% digitonin-buffer, and incubation with goat anti-human IgG or IgM conjugated with alkaline phosphatase for about 1 hour at room temperature (20° C). The wells will then be rinsed twice and the substrate added in substrate buffer. Following addition of stop buffer, the plate will be read on an ELISA plate reader. Controls will include wells with no antibody, normal sera, and HIV antibody from EIA/WB-positive sera.

If the early antibody significantly registers above normal control sera (i.e., at 4× or greater dilution) in this test, then this particular format will be employed in commercial embodiments. It is envisioned that further refinement may be made in the assay. In addition, more highly purified gp160 preparations will be prepared by affinity purification techniques well known to those of skill in the art, and used as target antigen in the detection of early anti-HIV antibody according to the present invention.

In the case that digitonin-solubilized material does not stick adequately to plastic plates, several other methods may be used. One method is to first coat the plates with an anti-gp41 or anti-gp 160 antibody, which would then immobilize gp 160 to the plastic in the presence of digitonin. This sandwich EIA also purifies the antigen during coating. Several other monoclonal antibodies may also be used to provide a first coating of antibody to the plates, such as e.g., monoclonal antibody to gp160, F105, or monoclonal antibody to gp41, chessie 8.

The present example describes the techniques and agents used to reduce background binding in the EIA of the present invention. A common problem with EIAs in the detection of human antibodies is the relatively high degree of background binding with normal control sera. Typically, normal sera needs to be diluted beyond 1:100 in order to be negative in the test as described here for HIV antibody. The following agents will be tested as blocking agents, either along or in combination:

Bovine serum albumin
PVP
Superblock

If high binding with control sera is still observed, other proteins which will not likely be seen by the human immune system, such as horse albumin, will be used. The blocking agent(s) that provide the lowest background binding will be selected and used in various embodiments of the method. Superblock is a commercially available blocking agent (Pierce Chemical) employed for blocking EIA plates.

Drying

The plates will first be dried to assess maintained reactivity with the early antibodies. Plates may alternatively be treated with a sucrose solution before drying to further enhance preservation of antigen conformational integrity. This technique has been used with other EIAs in order to maintain partial hydration of proteins. Alternatively, glycerin or gelatin may be used, which may preserve the antigen while partially dry, and then upon rehydration can be dissolved away as the first step in performing the assay. As yet another alternative, the plate wells may be kept wet and the plates well sealed to prevent leakage as a ready to use EIA tool.

The EIA will be tested against a panel of frozen, banked sera that were collected over a number of years from HIV-infected individuals, both sero-positive in the currently employed tests and early infected individuals who did not score in the current tests. Uninfected control sera will also be examined as controls. All of these will be tested undiluted or at various dilutions in the new EIA in order to determine optimal conditions for testing serum.

EXAMPLE 8

Development of Other GP160 Expressing Cell Lines

The present example outlines the method that will be used in the development of cell lines, such as CEM cell lines, that express recombinant HIV antigens. These cell lines will have early anti-HIV antibody reactivity. Exemplary recombinant HIV antigens will include those of the HIV strain 213, strain AC-1 and strain C. Cell lines infected with these recombinant antigens will express an antigen with early anti-HIV antibody detection activity similar to the HIV-infected cell lines developed and described here.

Restriction fragments from a human immunodeficiency virus may be obtained employing known restriction sites that flank nucleic acid sequence encoding the virus envelope protein, or an antigenically active fragment thereof. By way of example, the SalI-XhoI fragments from the particular HIV isolate, such as the $HIV_{AC-1}$ and $HIV_C$ described here, may be cloned in a suitable plasmid, such as the pUC19 plasmid. Restriction mapping may be used to confirm that the fragment encodes an HIV envelope protein according to the techniques well known to those of skill in the art. The obtained fragment may then be ligated into the cloning site of an appropriate vector, such as the pLNSX retrovirus vector (see FIG. 5). The retroviral vector will then be used to transfect an appropriate mammalian cell line, such as mink MiLu cells (ATCC CCL64) or any other line deemed appropriate. The cells may then be selected with a desired selection mechanism, such as antibiotic resistance, (e.g. 400–800 micrograms per ml of G418 for 1–2 weeks). Surviving cells from the selection procedure may then be cloned by limiting dilution in Terasaki plates. Individual clones may then be screened for expression of recombinant HIV gp160 by live-cell fluorescence (see Example 1) using monoclonal antibody F105 (Medarex, Anandale, N.J.). Clones that express the highest amount of recombinant antigen, based on fluorescence intensity measurements by flow cytometry, may be expanded and cell banks viably frozen.

The recombinant HIV antigens here described will be useful in the detection of early anti-HIV antibody, the antigen having conformational epitopes of the HIV antigen, and particularly HIV envelope antigen such as gp160, that are maintained and react with early anti-HIV antibodies. Non-live cell preparations of the HIV gp160 antigen are shown to maintain early anti-HIV antibody immunoreactivity using whole live cells infected with recombinant retroviral shuttle vectors carrying the gp160 gene fragment solubilized in digitonin. In some embodiments, whole cells infected with a retroviral vector carrying a nucleic acid fragment encoding gp160 will be solubilized in 1% digitonin and used to coat EIA plates. The gp160 expression product from HIV infected cell isolates, such as the $HIV_{213}$, may also be used in the described methods assay.

EXAMPLE 10

Comparative Tests of Recombinant HIV Protein Expressing Cells as Antigens vs Cells Infected with Live HIV Based Assays for Antibody For this study, sera from 41 longitudinally-studied high-risk individuals have been collected. Each serum was tested with the recombinant HIV antigen-expressing CEM cells in live cell immunofluorescence, as well as three commercially available EIAs for antibodies to HIV: Abbott Laboratories, Electronucleonics, and Organon-Technica. The assay procedures were those recommended by the manufacturers. Individuals who are found to be positive using the CEM lines, but negative in the three commercial assays, were identified.

PBLs samples obtained from each of these patients taken at the time of serum collection, will be analyzed by PCR for HIV DNA, as well as placed into culture and co-cultured with purified CD4 lymphocytes from normal donors. The latter is a very sensitive way of isolating HIV because it amplifies it. Therefore, subjects who are only positive in our test will have a confirmatory test of directly detecting HIV in the lymphocytes at the time of serum collection.

Data from these 41 subjects demonstrate that use of recombinant antigen expressing cells function to detect early anti-HIV antibody similar to HIV infected cells.

TABLE 10

Assesment of the Presence of "Early" Anti-HIV Antibodies by Live-Cell Immunofluorescence Using CEM Cells Expressing Recombinant gp160

| Serum | CEM | CEM-213env | CEM-AC1env | CEM-Cenv |
|---|---|---|---|---|
| Controls (1) | | | | |
| A | —* | — | — | — |
| B | — | — | — | — |
| C | — | — | — | — |
| D | — | — | — | — |
| E | — | — | — | — |
| F | — | — | — | — |
| HIV-infected EIA+/WB+ | | | | |
| HR-39 | — | 1200,640 | 1280,2500 | 640,640 |
| HR-49 | — | 1280,1280 | 1280,2400 | 640,1000 |
| HR-51 | — | 320,320 | 640,640 | 100,120 |
| HR-53 | — | 320,320 | 640,640 | 160,320 |
| R-410 | — | 640,1000 | 1280,1280 | 640,640 |
| HIV-infected High-risk EIA–/WB (2) | | | | |
| TL-1 | — | 60,80 | 100,80 | 40,40 |
| HR-2 | — | 40,50 | 20,40 | 30,20 |
| HR-9 | — | 60,80 | 20,20 | 20,20 |
| HR-22 | — | 40,40 | 60,80 | 10,20 |
| HR-48 | — | 50,40 | —,— | 10,10 |
| HR-55 | — | 100,120 | 20,40 | 20,20 |
| HR-56 | — | 80,100 | 40,50 | 40,40 |

*(—) = No reactivity at 1:10 or higher dilutions of serum. Data expressed as reciprocal of serum dilution that stained 50% of cells.
(1) Uninfected low-risk subjects whose sera was negative for "Early" anti-HIV antibody by live-cell immunofluorescence using cells acutely infected with HIV
(2) Sera positive for "Early" anti-HIV antibody by live-cell immunofluorescence using cells acutely infected with HIV

EXAMPLE 11

Live- or Fixed-Cell EIA's

The present example demonstrates a particularly envisioned embodiment of the assay plates of the present invention that employ live recombinant cells that express the desired HIV envelope antigen as a target antigen. These recombinant live cells may be adhered to the wells of the plate through a variety of different mechanisms, such as by use of cell lines that must attach to a substrate to grow.

Particular embodiments of these plates include live- or fixed-cell EIAs in which the wells are plated with live cells expressing the envelope proteins of HIV strains 213, AC-1, or C. These live cells would attach to plastic plates. Cell lines that grow by adhering to a substrate include mink lung fibroblasts (MiLu) as well as other fibroblastic or epithelial cell lines from human or various animal species. The cells would be infected with amphotropic MuLV packaged retrovirus containing the envelope genes of one or any combination of the virus strains noted above. The cells would then be selected for G418 resistance. The selected cells will then be individually cloned and the clones expressing the highest levels of envelope proteins as assessed by live-cell immunofluorescence, will be used in the EIA. For the EIA, the cells will be plated into 96-well flat bottom microtiter plates and allowed to attach and grow to confluency.

The plate can be used with the live cells, or alternatively, the cells can be fixed with a mild fixative (e.g., 0.5% glutaraldehyde) that would not destroy the conformational epitopes of gp160 necessary for detecting early anti-HIV antibodies. Dilutions of test sera as well as known positive and negative control sera, will be added to individual wells, allowed to incubate for 1–2 hr., and then removed. The wells will then be washed 3–5× with PBS. A secondary antisera conjugated with an enzyme (e.g., alkaline phosphase) will then be incubated in each well for 1–2 hr., followed by three rinses with PBS. Substrate will then be added to the wells until a visible color is detected. The plate will then read on an EIA plate reader employing techniques well known to those of ordinary skill in the art.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Steckelberg, J. M. and Cockerill, III, F. R., *Mayo Clin. Proc.*, 63:373–380, 1988.
2. Schleupner, C. J., *Prin. & Practice of Infectious Diseases—Update I*, 10:3–19, 1989.
3. Salahuddin, S. A., Markham, P. D., Redfield, R. R., et al., *Lancet*, 2:1418–1420, 1984.
4. Mayer, K. H., Stoddard, A. M., McCusker, J. Avofte, D., et al., *Ann. Intern. Med.*, 104:194–196, 1986.
5. Ranki, A., Valle, S. L., Krohn, M., Antonene, J. Allain, J. P., Leuther, M., et al., *Lancet*, 2:589–593, 1987.
6. Imagawa, D. T., Lee, M. H., Wolinsky, S. M., Sano, K., et al., *N. Eng J. Med.*, 320:1458–1462, 1989.
7. Aiuti, F., Ensoli, F., Fiorelli, V., Mezzaroma, I., Pinter, E., Guerra, E., et al., *Vaccine*, 11:538–541, 1993.
8. Gorrino, M. T., Campelo, C., Suarez, M. D., et al., *Eur. J. Clin. Micro. & Infect. Dis.*, 13:271–276, 1994.
9. Pezzella, M., Rosci, M. A., Miceli, M. Vonesch, N., et al., *J. Medical Virology*, 35:14–18, 1991.
10. Brettler, D. B., Somasundaran, M., Forsberg, A. F., Krause, E., et al., *Blood*, 80:2396–2400, 1992.
11. Gupta, P., Kingsley, L., Anderson, R., Ho, M., Enrico, A., Ding, M., et al., *AIDS*, 6:143–149, 1992.
12. Luque, F., Leal, M., Pineda, J. A., Torres, Y., et al., *Eur. J. Clin. Micro. & Infect. Dis.*, 12:663–667, 1993.
13. Eble, B. E., Busch, M. P., Khayam-Bashi, H., et al., *Transfusion*, 32:503–508.
14. Sheppard, H. W., Busch, M. P., Louis, P. H., et al., *J. Acq. Imm. Def. Syn.*, 6:1339–1346, 1993.
15. Coutlee, F., Oliver, C., Cassol, S., Voyer, H., Kessous-Elbaz, A., et al., *Amer. J. of Med.*, 96:42–48, 1994.
16. Yerly, S., Chamot, E., Deglon, J. J., Hirschel, B., et al., *J. Infectious Diseases*, 164:965–968, 1991.
17. Pan, L. Z., Sheppard, H. W., Winkelstein, W. and Levy, J. A., *J. Infectious Diseases*, 164:963–964, 1991.
18. Busch, M. P., Lee, L. L., Satten, G. A., Henrard, D. R., Farzadegan, H., et al., *Transfusion*, 35:91–97, 1995.
19. Celum, C. L., Coombs, R. W., Lafferty, W., L=Inui, T. S., et al., *J. Infect. Dis.*, 164:656–664, 1991.
20. Pepose, J. S., Buerger, D. G., Paul, D. A., Quinn, T. C., et al., *Opthalmology*, 99:879–888, 1992.
21. Stramer, S. L., Heller, J. S., Coombs, R. W., Ho, D. D. and Allain, J. P., *N. Eng J. Med.*, 319:513–514, 1988.
22. Ward, J. W., Holmberg, S. D., Allen, J. R., Cohn, D. L., et al., *N. Engl. J. Med*, 318:473–478, 1988.
23. Cohen, N. D., Munoz, A, Reitz, B. A., Ness, P. K., et al., *N. Engl. J Med.*, 320:1172–1176, 1989.
24. Simonds, R. J., Holmberg, S. D., Hurwitz, R. L., et al., *N. Engl. J. Med.*, 326:726–732, 1992.
25. Ward, J. W., *Developments in Biological Standardization*, 81:41–43, 1993.
26. Busch, J. P., Young, M. J., Samson, S. M., Mosley, J. W., et al., *Transfusion*, 31:4–11, 1991.
27. Patijn, G. A., Strenger, P. F., and Persijn, G., *Transplant International*, 6:165–172, 1993.
28. Clerici, M., Berzofsky, J. A., Shearer, G. M., and Tacket, C. O., *J. Infect. Dis.*, 164:178–182, 1991.
29. Clerici, M., Levin, J. M., Kessler, H. A., Harris, A., Berzofsky, J. A., et al., *JAAM*, 271:42–46, 1994.
30. Jehuda-Cohen, T., Slade, B. A., Powell, J. D., et al., *Proc. Natl. Acad. Sci., USA*, 87:3972–3976, 1990.
31. Race, E. M., Ramsey, K. M., Lucia, H. L. and Cloyd, M. W., *Virology*, 184:716–722, 1991.
32. Cloyd, M. W. and Holt, M. J., *Virology*, 161:286–292, 1987.
33. Muller, S., Richalet, P., Laurent-Crawford, A., Barakat, S., Riviere, Y., et al., *AIDS*, 6:933–942, 1992.
034. Centers for Disease Control, *MMWR*, 36:225–236, 1987.
35. Weiblen, B. J., Lee, F. K., Cooper, E. R., et al., *Lancet*, i:988–990, 1990.
36. Martin, N. L., Levy, J. A., Legg, H., et al., *J. Pediatrics*, 118:354–358, 1991.
37. Garbarg-Chenon, A., Segondy, M., Conge, A. M., et al., *J. of Virological Methods*, 42:117–125, 1993.
38. Anonymous, *J. of Acquired Immune Deficiency Syndromes*, 5:1169–1178, 1992.
39. Heredia, A., Hewlett, I. K., Soriano, V., and Epstein, J. S., *Transfusion Med. Reviews*, 8:223–231, 1994.
40. Cozzi Lepri, A., Pezzotti, P. Dorrucci, M., Phillips, A. N., and Rezza, G., *BMJ*, 309:1537–1542, 1994.
41. McNulty, A., Kaldor, J. M., McDonald, A. M., et al., *BMJ*, 308:825–826, 1994.
42. Cloyd, M. W., Hartley, J. W., and Rowe, W. P., *J. Exptl. Med.*, 149:702–712, 1979.
43. Chesbro, B., Wehrley, K., Cloyd, M., Britt, W., Portis, J., Collins, J. and Nishio, J., *J. Virology*, 112:131–144, 1981.
44. Cloyd, M. W., Chesebro, B., Portis, J. L. and Weir, M., *J. Virol.*, 41:1112–1117, 1981.
45. Portis, J. L., McAtee, F. J., and Cloyd, M. W., *Virology*, 118:181–190, 1982.
46. Chesbro, B., Britt, W., Evans, L., Wehrly, K., Nishio, J. and Cloyd, M., *Virology*, 127:134–148, 1983.
47. Kyte & Doolittle (1982) *J. Mol. Biol.* 157:105–132.
48. Sambrook et al. (1989). *Molecular cloning: A laboratory manual*. Cold Spring Harbor Laboratory. Cold Spring Harbor, N.Y.

What is claimed is:

1. A natural or recombinant human immunodeficiency virus envelope protein antigen capable of binding an early anti-HIV antibody not detected by conventional immunodiagnostic assays, wherein said protein has been extracted with digitonin or nonylphenoxy polyethoxy ethanol (NP40), has a molecular weight of about 160,000 Daltons as determined by SDS/PAGE, and has been obtained from HIV-infected or recombinant vector transfected eukaryotic cell extracts.

2. The protein of claim 1 further defined as prepared by a process comprising:
preparing a restriction fragment comprising human immunodeficiency virus nucleic acid encoding an envelope protein gp 160;
inserting said restriction fragment into a vector capable of expressing in a eukaryotic cell;
transfecting a eukaryotic cell with said recombinant vector; and collecting a recombinant protein capable of binding an early anti-HIV antibody.

3. The recombinant protein of claim 1 wherein the eukaryotic cell is mammalian.

4. The recombinant protein of claim 1 wherein the eukaryotic cell is CEM or Mu-1-Lu.

5. The recombinant protein of claim 1 wherein the recombinant vector is pLNSX-env.

6. A recombinant human immunodeficiency virus envelope protein antigen which is capable of binding an early anti-HIV antibody not detected by conventional immunodiagnostic assays, wherein said protein has been extracted with digitonin or nonylphenoxy polyethoxy ethanol (NP40) and is produced by a eukaryotic cell transfected with a vector comprising a nucleic acid molecule having a sequence encoding a human immunodeficiency virus gp160 protein.

7. A recombinant human immunodeficiency virus envelope protein antigen which is capable of binding an early anti-HIV antibody not detected by conventional immunodiagnostic assays, wherein said protein has been extracted with digitonin or nonylphenoxy polyethoxy ethanol (NP40) and is produced by a mammalian cell comprising a recombinant vector including a sequence encoding a human immunodeficiency virus (HIV) gp160 protein.

8. The recombinant protein of claim 7, wherein the sequence encoding an HIV gp160 protein is a SalI-XhoI restriction fragment from $HIV_{213}$, $HIV_{AC-1}$, or a combination thereof.

9. The recombinant protein of claim 7 wherein the mammalian cell is further defined as a CEM or Mu-1-Lu cell.

10. The recombinant protein of claim 7, wherein the sequence encoding a gp160 HIV protein is an SalI-XhoI restriction fragment from $HIV_{213}$ (ATCC VR2247).

11. A target antigen preparation comprising a recombinant HIV envelope protein gp160 that is capable of binding to an early anti-HIV antibody not detected by conventional immunodiagnostic assays wherein said protein has been extracted with digitonin or nonylphenoxy polyethoxy ethanol (NP40) and is obtained from a purified eukaryotic cell lysate, said eukaryotic cell lysate comprising a lysate from HIV infected mammalian cells, said cells being infected with $HIV_{AC-1}$ or $HIV_{213}$.

12. The target antigen of claim 11 wherein the mammalian cell lysate is prepared by a process of solubilizing the HIV expressing mammalian cells with about 0.1% to an about 10% digitonin.

13. The target antigen of claim 11, wherein the mammalian cells are CEM cells.

14. The target antigen of claim 11, wherein the mammalian cells are Mu-1-Lu cells.

* * * * *